(12) United States Patent
Walker et al.

(10) Patent No.: US 11,387,001 B2
(45) Date of Patent: Jul. 12, 2022

(54) MEDICAL INTERVENTION CONTROL SYSTEM

(71) Applicant: THALAMUS AI LIMITED, Birmingham (GB)

(72) Inventors: Jeremy James Walker, Birmingham (GB); Justin Davies, Birmingham (GB)

(73) Assignee: THALAMUS AI LIMITED, Birmingham (GB)

( * ) Notice: Subject to any disclaimer, the term of this patent is extended or adjusted under 35 U.S.C. 154(b) by 75 days.

(21) Appl. No.: 16/957,044

(22) PCT Filed: Dec. 21, 2018

(86) PCT No.: PCT/GB2018/053745
§ 371 (c)(1),
(2) Date: Jun. 22, 2020

(87) PCT Pub. No.: WO2019/122919
PCT Pub. Date: Jun. 27, 2019

(65) Prior Publication Data
US 2020/0395126 A1 Dec. 17, 2020

(30) Foreign Application Priority Data
Dec. 21, 2017 (GB) ..................... 1721581

(51) Int. Cl.
*G16H 50/30* (2018.01)
*G16H 40/67* (2018.01)
*G16H 50/20* (2018.01)
*A61B 5/00* (2006.01)

(52) U.S. Cl.
CPC .......... *G16H 50/30* (2018.01); *A61B 5/7235* (2013.01); *G16H 40/67* (2018.01); *G16H 50/20* (2018.01)

(58) Field of Classification Search
USPC ........................................................ 705/2–3
See application file for complete search history.

(56) References Cited

U.S. PATENT DOCUMENTS

2004/0078236 A1* 4/2004 Stoodley ................ G16H 70/20
705/2
2007/0244724 A1* 10/2007 Pendergast ............. G16H 50/70
600/300
(Continued)

FOREIGN PATENT DOCUMENTS

EP 0917078 A1 5/1999

OTHER PUBLICATIONS

Wiens, et al., "Patient Risk Stratification with Time-Varying Parameters: A Multitask Learning Approach", Journal of Machine Learning Research, vol. 17, pp. 1-23, 2016. (Year: 2016).*
(Continued)

*Primary Examiner* — Amber A Misiaszek
(74) *Attorney, Agent, or Firm* — Michael G. Monyok

(57) ABSTRACT

A medical intervention control system for providing a risk analysis and influencing intervention action on a patient, the system comprising: a database with a data set containing data from at least one data source comprising: a) study data; and b) sensed data; a waveform detector operable to identify a waveform from a data source, extract the waveform, categorise the waveform, normalise the waveform to a predetermined format and determine waveform characteristics and parameters of the waveform, the waveform detector populating part of the sensed data; a measurement module to derive subject data from the patient; an analyser operable to analyse the subject data with respect to the data set from the at least one data source and output an associated probability for each of one or more outcomes, wherein the associated probability is affected by an intervention, wherein the analyser takes subject data derived from the patient and tests for outcomes and potential interventions which influence the outcomes; an action and alert management module to provide feedback to an intervention allocation module and, for respective interventions, being operable to output a direct (Continued)

instruction to an intervention allocation module to perform an intervention or a direct instruction to an intervention allocation module to desist from performing an intervention; and an intervention allocation module to perform an intervention or desist from an intervention depending on the direct instruction from the action and alert management module on the current patient.

16 Claims, 26 Drawing Sheets

(56) References Cited

U.S. PATENT DOCUMENTS

| | | | |
|---|---|---|---|
| 2008/0294019 A1* | 11/2008 | Tran | G16H 40/63 600/301 |
| 2009/0054908 A1* | 2/2009 | Zand | A61B 5/7455 600/300 |
| 2014/0108045 A1 | 4/2014 | Afshar | |
| 2015/0255004 A1 | 9/2015 | Manzke | |
| 2016/0055307 A1 | 2/2016 | Macoviak | |
| 2017/0231701 A1 | 8/2017 | Cohen | |

OTHER PUBLICATIONS

International Search Report and Written Opinion of the International Searching Authority for PCT Application PCT/GB2018/053745 dated Jun. 23, 2020.

* cited by examiner

Model predicts: 17% chance of event

MEDICAL INTERVENTION CONTROL SYSTEM

CROSS-REFERENCE TO RELATED APPLICATIONS

This application is a national stage entry under 35 USC § 371 of international application no. PCT/GB2018/053745, filed Dec. 21, 2018, which claims priority to foreign application no. GB 1721581.5, filed on Dec. 21, 2017, each of which is incorporated herein by reference.

This invention relates to a medical intervention control system for providing a risk analysis and influencing intervention action on a patient.

BACKGROUND

In the medical healthcare field there is much reliance on personal consultation with a medical professional to determine a data set for a patient/subject and subsequent analysis of the patient/subject data by one or more medical professionals to determine what outcomes may be expected and what risks may be associated with respective interventions or courses of action (or inaction) in order to make a decision about beginning an intervention or appreciating that the best outcome can be achieved by doing nothing and not performing a particular intervention.

Currently decisions made about the need to "treat" or "no treat" an arterial stenosis are based around specific data sources including pressure waveform, angiographic images, patient risk factors and demographics. In most cases, the analysis is confined to just one or other of these data sources, frequently using only a small segment for analysis and determination of the need for disease treatment. Such analysis formed much of the evidence base for the management of patients with coronary artery disease, but the decision-making is constrained by the limited amount of data available.

Multiple factors are involved when it comes to reviewing and deciding upon further treatment steps. For example in the coronary field, there are well known and developing risk factors which have been and are being identified and better understood. Risk factor categories in the coronary field include: blood pressure, total cholesterol, LDL cholesterol, and HDL cholesterol.

Gender is known to affect the risk factor and is taken into account when practitioners are assessing a patient and reviewing the cohort data and patient data. Ethnicity and age also affect the risk factor as do conditions such as diabetes. Lifestyle factors such as smoking also have an impact on risk factors. A medical professional has a large number of data sources available which provide study data on how these various factors influence treatment decisions and affect outcomes. Typically medical practitioners will have experience of a section of data particular to their experience, research area, practice location or patient base. For example, a New Zealand medical practitioner is more likely to have experience of risk factors in the Maori population which a medical practitioner in Scotland is less likely to have because of the different ethnicities.

The data sources available to practitioners and the data available from studies and research are available but usually in very different forms and the data does not fit readily into a standard template.

Despite the large body of information available to medical practitioners, current techniques for analysing risk associated with a medical event (such as an arterial stenosis) focus on usually a single index (such as Pd/Pa pressure) from a single data source (a pressure wire). Examples of such indexes for a measured pressure waveform are: FFR, iFR (instant wave-free ratio (iFR) version of FFR), coronary flow reserve—CFR, the relationship between resting distal coronary pressure to aortic pressure ratio (Pd/Pa), or from a derived waveform, QFR (quantitative flow ratio), or Heart-Flow (computational fluid dynamics modelling).

Such an index-focused review can mean that the risk analysis performed by the medical practitioner is overly based on the index data thereby skewing the risk analysis by not allowing for the effect of other risk factors.

Medical practitioners can be overwhelmed with the large body of study data available, the different scopes and foci of studies and the conflicting reports and conclusions that may arise. Medical practitioners may not be aware of recent developments or obscure developments affecting a particular group of patients and it would be possible for such developments to be overlooked.

Aspects of the present invention improve on this position and ameliorate disadvantages of known systems. Aspects of the invention are set out in the accompanying claims.

One aspect of the invention provides a medical intervention control system for providing a risk analysis and influencing intervention action on a patient, the system comprising:

a database with a data set containing data from at least one data source comprising: a) study data; and b) sensed data;

a waveform detector operable to identify a waveform from a data source, extract the waveform, categorise the waveform, normalise the waveform to a predetermined format and determine waveform characteristics and parameters of the waveform, the waveform detector populating part of the sensed data;

a measurement module to derive subject data from the patient;

an analyser operable to analyse the subject data with respect to the data set from the at least one data source and output an associated probability for each of one or more outcomes, wherein the associated probability is affected by an intervention, wherein the analyser takes subject data derived from the patient and tests for outcomes and potential interventions which influence the outcomes;

an action and alert management module to provide feedback to an intervention allocation module and, for respective interventions, being operable to output a direct instruction to an intervention allocation module to perform an intervention or a direct instruction to an intervention allocation module to desist from performing an intervention; and an intervention allocation module to perform an intervention or desist from an intervention depending on the direct instruction from the action and alert management module on the current patient.

Preferably, the analyser builds up a probability matrix trained to deliver a risk analysis of various "treat"/"no treat" options based on trained data and the system delivers a risk analysis of what the risk is if the patient is treated with an option or the risk if the patient is not treated with a treatment option.

Conveniently, the output of the action and alert management module includes a set of instructions relating to a respective intervention for the intervention allocation module.

Preferably, the intervention allocation module includes a medical robot operable to perform the intervention.

One aspect of the invention provides a method for providing a risk analysis and influencing intervention action on a patient, the method comprising:
- establishing a database with a data set containing data from at least one data source comprising: a) study data; and b) sensed data;
- populating part of the sensed data with waveform data, wherein the waveform is extracted from a data source and normalised to a predetermined format;
- deriving subject data from the patient;
- testing the subject data for outcomes and potential interventions which influence the outcomes for the patient;
- analysing the subject data with respect to the data set from the at least one data source and outputting an associated probability for respective outcomes, wherein the associated probability is affected by an intervention;
- outputting, for respective interventions, a direct instruction to perform an intervention or a direct instruction to desist from performing an intervention; and
- performing the intervention or desisting from the intervention depending on the direct instruction.

Another aspect of the present invention provides a medical intervention control system for providing a risk analysis and influencing intervention action on a patient, the system comprising:
- a database with a data set containing data from at least one data source comprising: a) study data; and b) sensed data;
- a waveform detector operable to identify a waveform from a data source and determine waveform characteristics and parameters of the waveform,
- a measurement module to derive subject data from the patient;
- an analyser operable to analyse the subject data with respect to the data set from the at least one data source and output an associated probability for each of one or more outcomes, wherein the associated probability is affected by an intervention, wherein the analyser takes subject data derived from the patient and tests for outcomes and interventions;
- an action and alert management module operable to provide feedback to a treatment allocation module; and
- an intervention allocation module to influence intervention or lack of intervention on the current patient.

Another aspect of the present invention provides a medical intervention control system for providing a risk analysis and influencing intervention action on a patient, the system comprising:
- a database with a data set containing data from at least one data source;
- a measurement module to derive subject data from the patient;
- an analyser operable to analyse the subject data with respect to the data set from the at least one data source and output an associated probability for each of one or more outcomes, wherein the associated probability is affected by an intervention.

Preferably, the analyser builds up a probability matrix trained to deliver a risk analysis of various "treat"/"no treat" options based on trained data and the system delivers a risk analysis of what the risk is if the patient is treated with an option or the risk if the patient is not treated with a treatment option.

Conveniently, the at least one data source comprises: a) study data; and b) sensed data; and the study data comprises: historic data which includes patient risk factors, patient demographics, associated clinical outcomes and results, historic sensed data and medical insurance profiles or social media feeds, Registry data; Actuarial risk tables; Clinical trial data; and/or Audit data; and the sensed data comprises: captured or sensed data points, waveforms or images obtained from sensing equipment such as electrocardiograms, coronary pressure wires and transducers, angiograms, ultrasonic transducers, coronary guidewire-mounted sensors to provide data on Fractional Flow Reserve—FFR, iFR (instant wave-free ratio (iFR) version of FFR), coronary flow reserve—CFR, the relationship between resting distal coronary pressure to aortic pressure ratio (Pd/Pa), medical insurance profiles and/or social media feeds.

Preferably, probability node values from each input are run in a matrix, where each value is iterated by further input from the fields to determine a series of probability node values for each of the inputs when used individually or when used in consort with other inputs and the series of node values determine the need for treatment, the probability of significant mortality and morbidity, risk analysis and the ability to discriminate between focal and diffuse disease and a probability is assigned to each outcome or potential intervention so as to then make a determination, potentially in consultation with a health professional or to better inform the practicing health professional about what outcomes or interventions to consider.

Another aspect of the present invention provides a method of providing a risk analysis and influencing intervention action on a patient, comprising:
- establishing a database with a data set containing data from at least one data source comprising: a) study data; and b) sensed data;
- identifying a waveform from a data source;
- determining waveform characteristics and parameters of the waveform,
- deriving subject data from the patient;
- analysing the subject data with respect to the data set from the at least one data source;
- outputting an associated probability for each of one or more outcomes, wherein the associated probability is affected by an intervention;
- testing the subject data for outcomes and interventions;
- providing feedback and influencing intervention or lack of intervention on the patient.

A further aspect of the present invention is a method of providing a risk analysis and influencing intervention action on a patient, comprising:
- establishing a data set containing data from at least one data source;
- deriving subject data from the patient;
- analysing the subject data with respect to the data set from the at least one data source;
- outputting an associated probability for each of one or more outcomes, wherein the associated probability is affected by an intervention.

Another aspect of the present invention provides a computer operable medium programmed with a set of instructions to:
- identify a waveform from a data source;
- determine waveform characteristics and parameters of the waveform,
- derive subject data from the patient;
- analyse the subject data with respect to data from at least one data source comprising: a) study data; and b) sensed data;

output an associated probability for each of one or more outcomes, wherein the associated probability is affected by an intervention;

test the subject data for outcomes and interventions;

provide feedback and influence intervention or lack of intervention on the patient.

A further aspect of the present invention is a computer operable medium programmed with a set of instructions to:

derive subject data from the patient;

analyse the subject data with respect to data from at least one data source comprising: a) study data; and b) sensed data;

output an associated probability for each of one or more outcomes, wherein the associated probability is affected by an intervention.

In order that the present invention can be more readily understood, embodiments of the invention will now be described, by way of example, with reference to and as shown in the accompanying drawings, in which.

Figure 25:
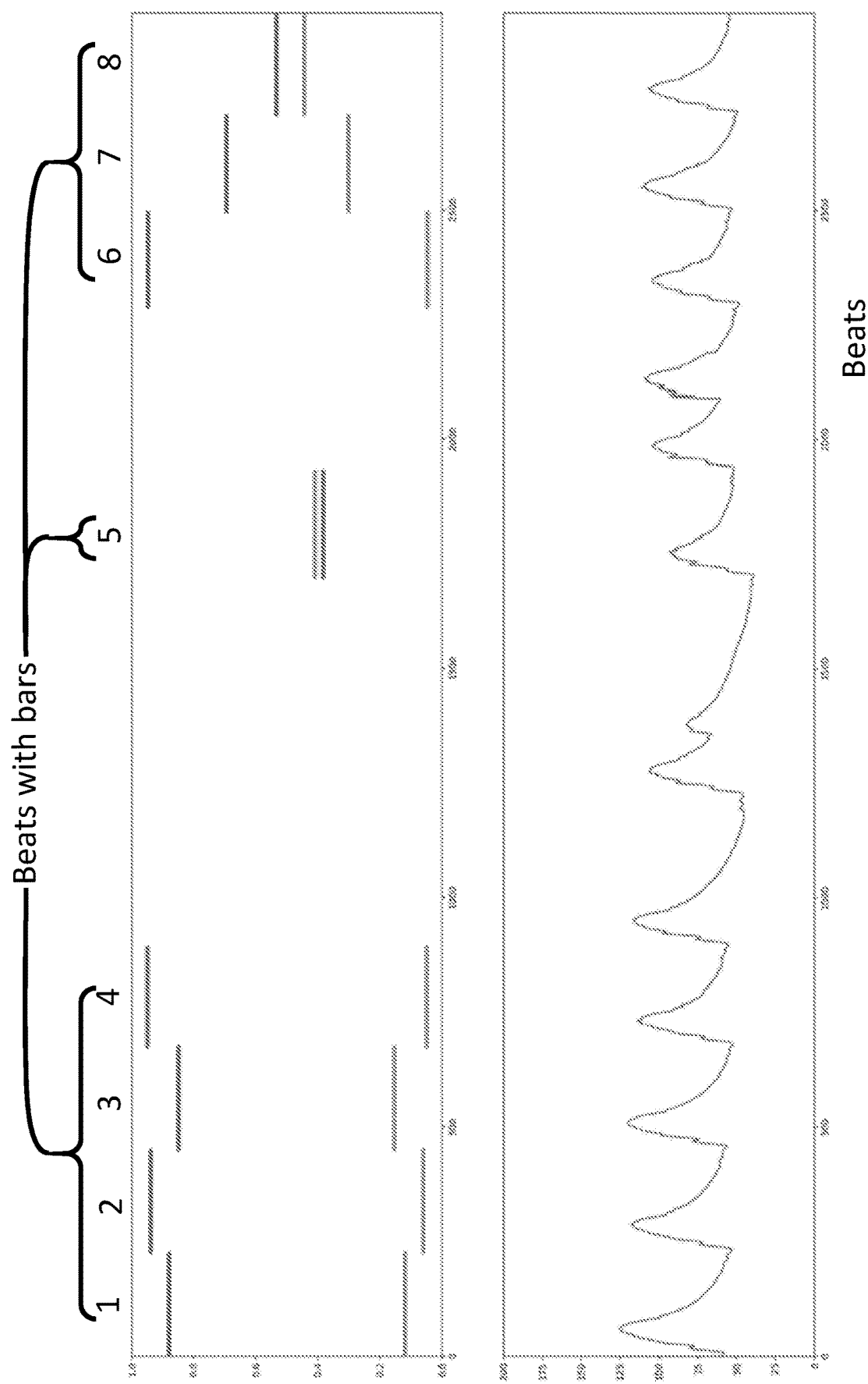
Figure 26:
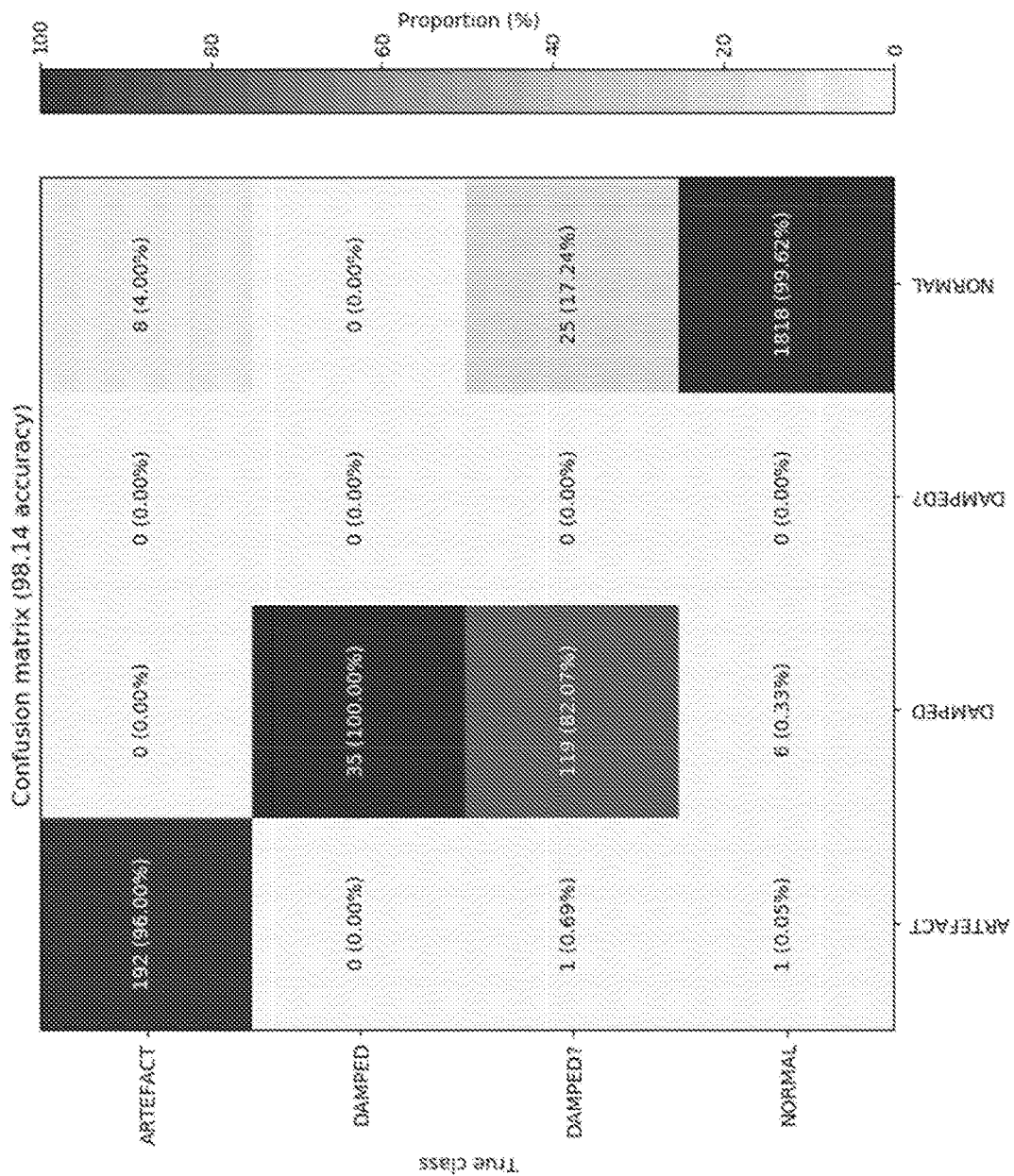

The lower panel of FIG. 25 shows each beat obtained from a pressure sensing catheter;

The upper panel of FIG. 25 shows the % likelihood of respective beats being normal and damped; and FIG. 26 shows the accuracy of a control system embodying the invention predicting the nature of beats.

Figure 1:
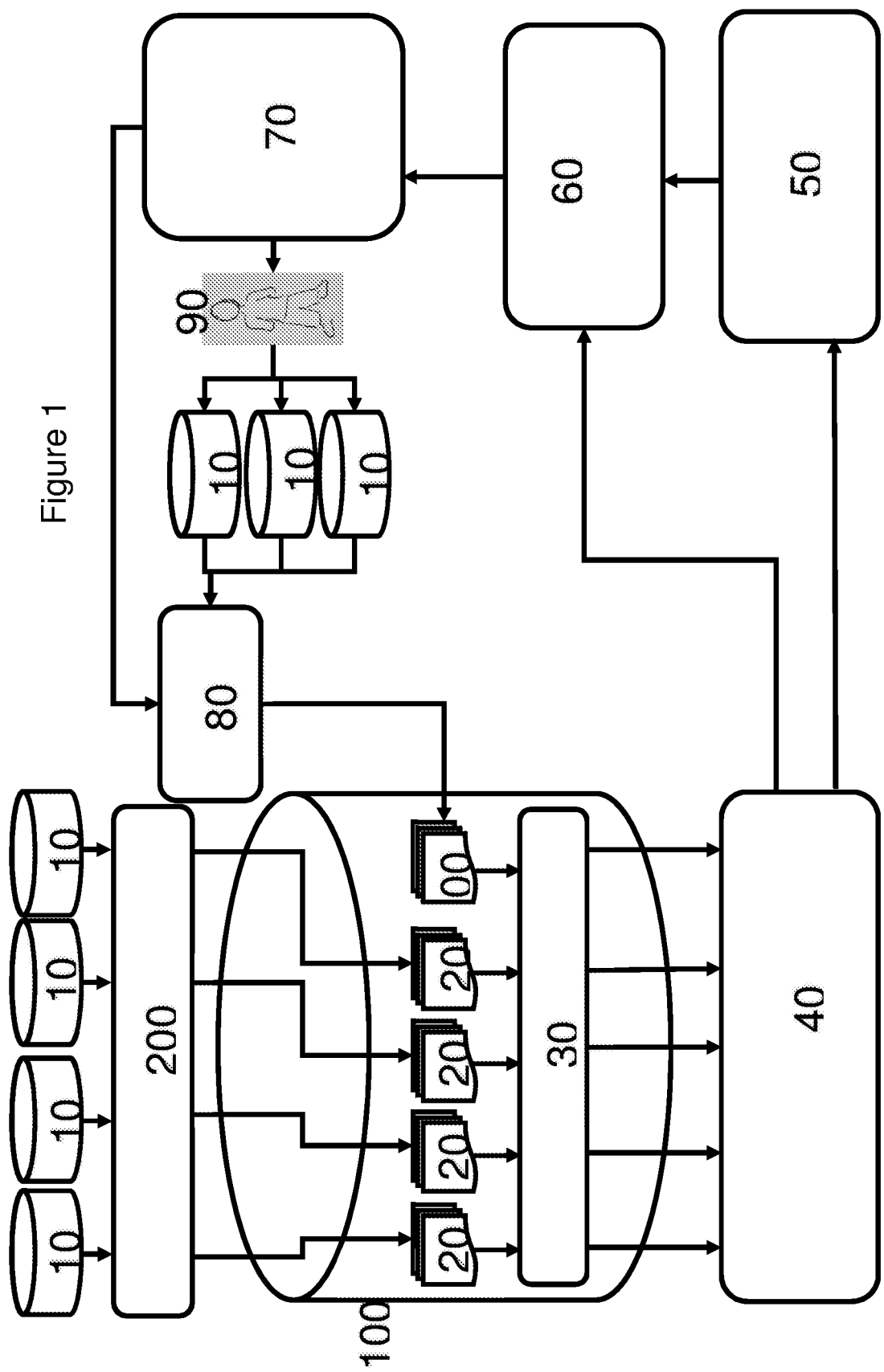
FIG. 1 is a schematic representation of a system embodying the present invention.

Referring to FIG. 1, a system 1 is disclosed which comprises a medical intervention control system 1 for providing a risk analysis and influencing intervention action on a patient, the system 1 comprising: a database 100 containing a data set containing data 20 from one or more data sources or sensors 10 and likely outcomes 30; subject data 00 in respect of a current patient 90; an analyser 40 operable to analyse the subject data 00 with respect to the data set 100 and output one or more likely outcomes, each with an associated probability; a risk analysis assessment module 50 operable to provide a risk analysis based on the output of the analyser; an action and alert management module 60 operable to provide feedback to an intervention or treatment allocation module 70; the intervention allocation module 70 to influence intervention or lack of intervention on the current patient 90; and a measurement module 80 to derive subject data 00 from the current patient 90.

The system 1 of FIG. 1 shows a feedback loop with controls in place to analyse captured data and train the analyser 40 from the data being captured. The captured data populates a data set in the database 100. The database comprises all viable data previously captured and analysed (the evidence base) and output a predictive model to inform next steps by a surgeon, for example. The next steps may indicate a particular intervention would have a probability of a good outcome or may indicate that the best outcome is non-intervention. The intervention allocation module 70 implements (or not) the intervention under command of the action and alert management module 60. The captured data 20 comprises inputs for predictive models in the analyser 40.

The system can suggest one or more potential interventions which may have an effect on the outcomes. The system identifies particular interventions which are likely to be beneficial and/or identifies particular interventions which are not likely to be beneficial. The system can associate probabilities (or risk levels) with respective interventions. The system can also include intervention parameters or further instructions into the output of the predictive model. For example, if a likely beneficial intervention is the insertion of a stent, then the predictive model can suggest an optimal location in the cardiac space for a stent, the type of stent and the dimensions of the stent and an optimal path to deploy the stent.

In some embodiments, the output of the predictive model is a direct instruction to the intervention allocation module to perform a particular intervention or procedure or a direct instruction to desist from performing a particular intervention or procedure. The intervention or procedure is preferably a procedure performed by a medical robot, either fully autonomous or partly autonomous. The output of the predictive model can include a set of instructions relating to an identified intervention or procedure.

The intervention allocation module 70 may include a medical robot 70 or may provide instructions to a medical robot which may be proximal or remote to the intervention allocation module 70.

Further, the system can also function as a closed loop, sensing data from the patient before, during an ongoing intervention and/or after the intervention is complete. The data sensed from the patient at these different stages of an intervention is used to send further refreshed instructions for implementation, preferably by a medical robot.

In the case of a robot 70 performing an intervention under instruction from a control system embodying the invention, the robot can follow the instructions or recommendations, and, for example, deploy the stent or reposition the catheter in response to changed sensed data from the patient—for example, the waveform from the patient may have become damped. By including the robot in the control system, real-time or close to real-time adjustments can be made to the intervention by the control system embodying the present invention. The control system embodying the present invention enables implementation of a dynamic process.

The control system embodying the present invention may also involve manual input from and/or notification to a human user such as a medical practitioner or authorised operative of either a medical robot or other surgical equipment. For example, the control system provides direct instructions to a medical practitioner who may be required by the control system to authorise or confirm one or more procedural steps in the respective intervention. Without involvement or authorisation from the medical practitioner or authorised operator, the procedural steps or the intervention itself cannot be performed. This provides both oversight and helps to improve patient safety.

Figure 24:
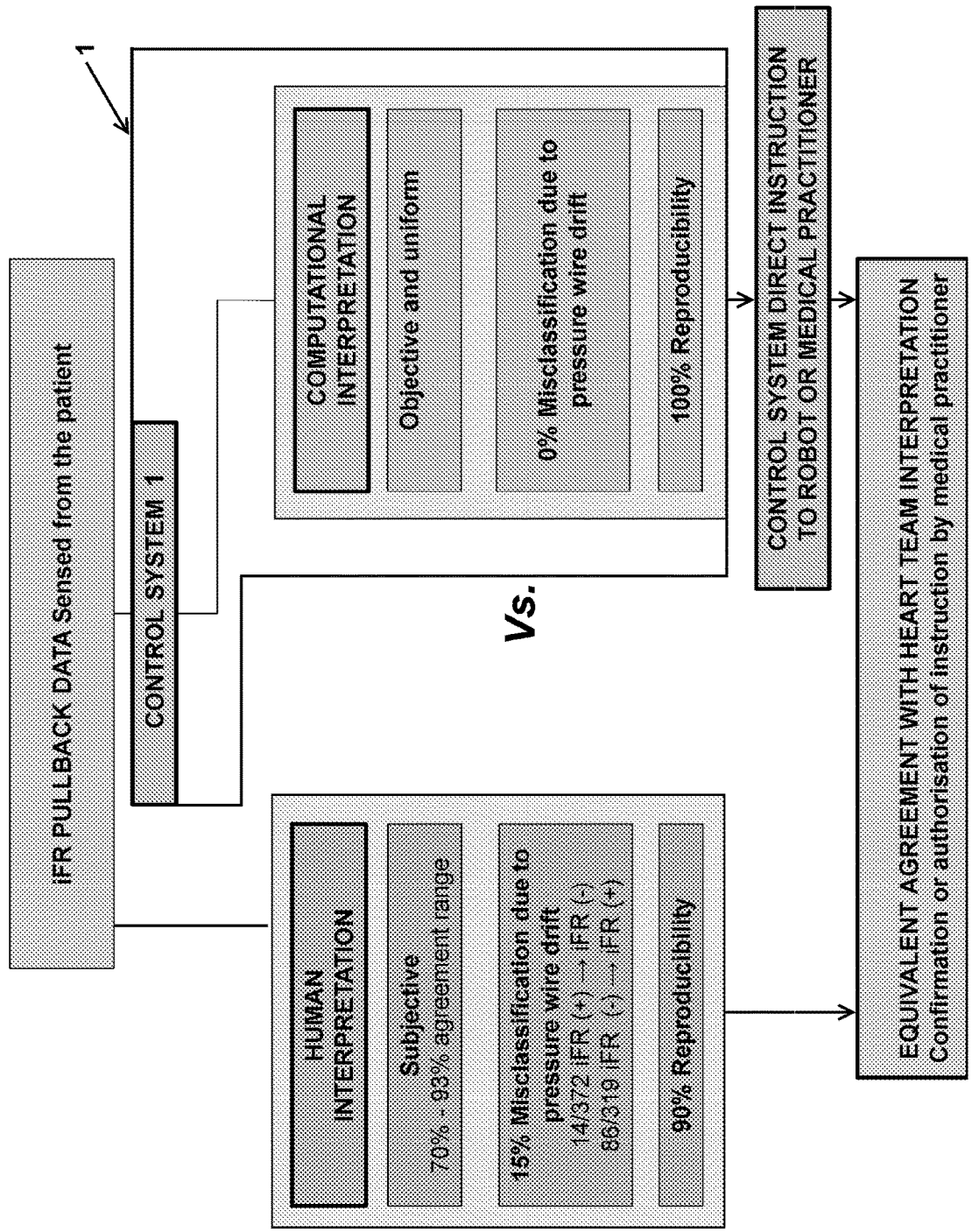
FIG. 24 shows the control system embodying the present invention operating with pullback data sensed from a patient.

The control system embodying the present invention helps to improve patient safety. Further, having a medical practitioner or authorised operator monitoring the progress of the intervention by using a control system embodying the present invention helps to improve safety. The control system may provide the practitioner/operator with access to computational interpretation of the data sensed from the patient and image data from the patient—the practitioner is informed by both their own personal experience and also by the computational interpretation provided by the control system 1 embodying the present invention. FIG. 24 shows an example of the control system embodying the present invention reviewing iFR pullback catheter data from a patient in parallel with a human interpretation of the same sensed data but without the benefit of the control system's computational insight.

In the example of FIG. 24, the control system is reviewing the pullback data from a pressure sensing catheter in the patient. The lower panel of FIG. 25 shows each beat obtained from the pressure sensing catheter. The upper panel of FIG. 25 shows the % likelihood of normal (darker bars uppermost (L to R) in bar sets 1,2,3,4,6,7&8), and the % likelihood of damped (lighter bars uppermost (L to R) $5^{th}$ set only) thus delivering a likelihood of individual beats being normal or damped. FIG. 26 shows the accuracy of control systems embodying the invention predicting Artefact, Damped, Potentially Damped and Normal beats. The model behind FIG. 26 was generated from the database 100 (containing study data and/or clinical data) and including a dataset where artefact, damped, potentially damped and normal beats had been pre-defined (true class). This was then tested against a further dataset of real world clinical data of over 5000 beats. The resultant model was shown to be highly accurate (98.14%) for predicting the true class, and over 99% accurate for determining normal beats, and 100% accurate for determining damped beats.

Referring again to FIG. 24, the practitioner is reviewing the pullback data during the intervention. The control system 1 is also reviewing the pullback data and identifies that waveforms have transitioned from normal (bars 1 to 4 in FIG. 25) and are now damped (bar 5 in FIG. 25). The control system 1 is instantly aware of the transition from normal to damped and sends a direct instruction to the medical practitioner or robot (in this case a pullback motor operable to retract the catheter and/or pullback wire) to withdraw the catheter to a safe position. Patient safety is at risk if the damped waveforms are allowed to persist. Withdrawing the catheter promptly can prevent or alleviate patient safety concerns such as the heart being starved from blood, chest pain, arrhythmias or cardiac arrest.

Figure 10:
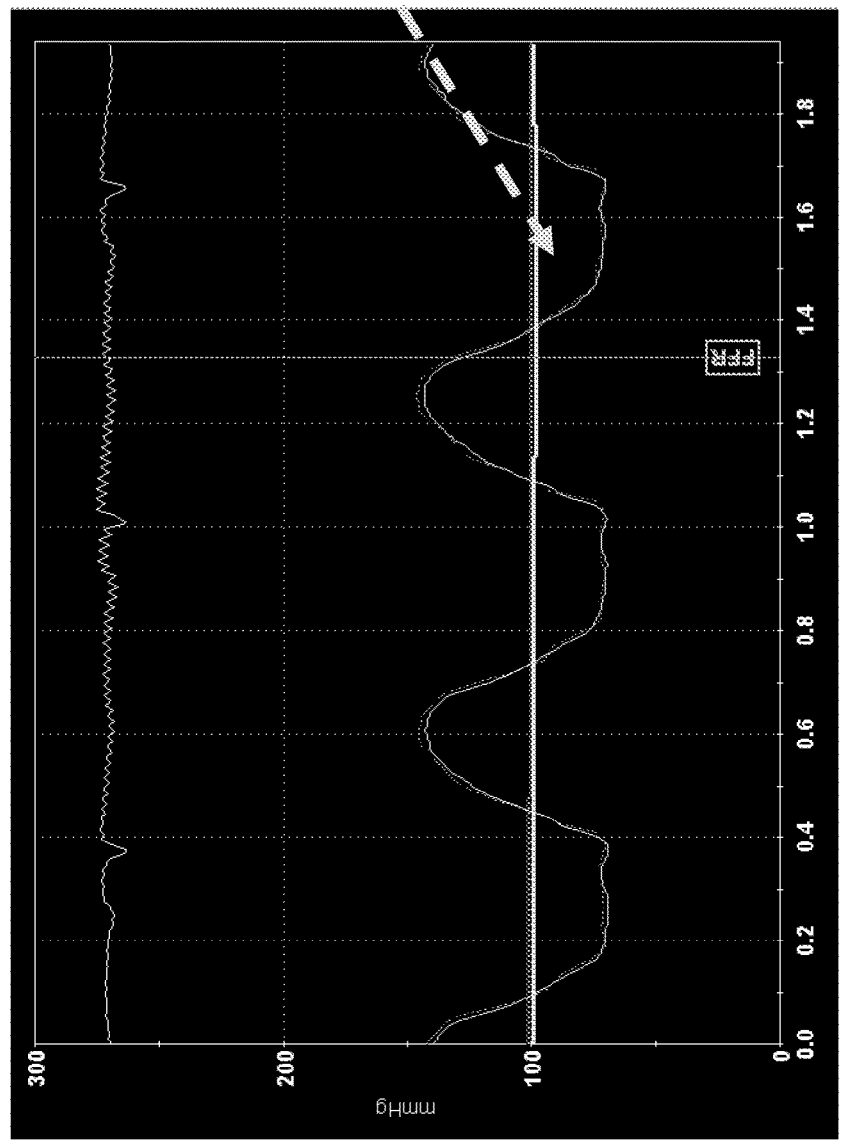
FIG. 10 is a trace of a series of pressure waveforms showing damping artefacts.
Figure 11:
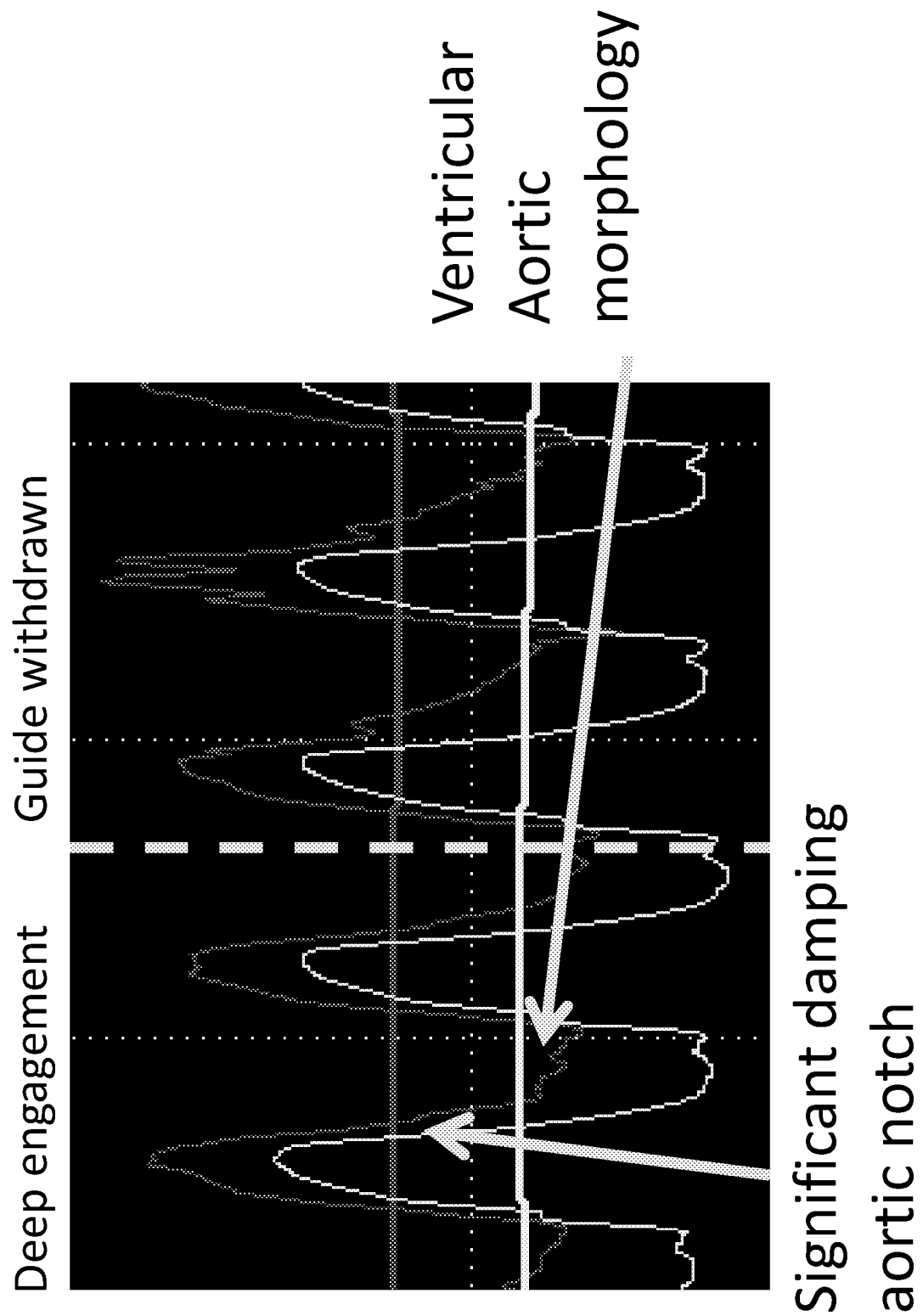
FIG. 11 is a pressure waveform trace having characteristics.
Figure 12:
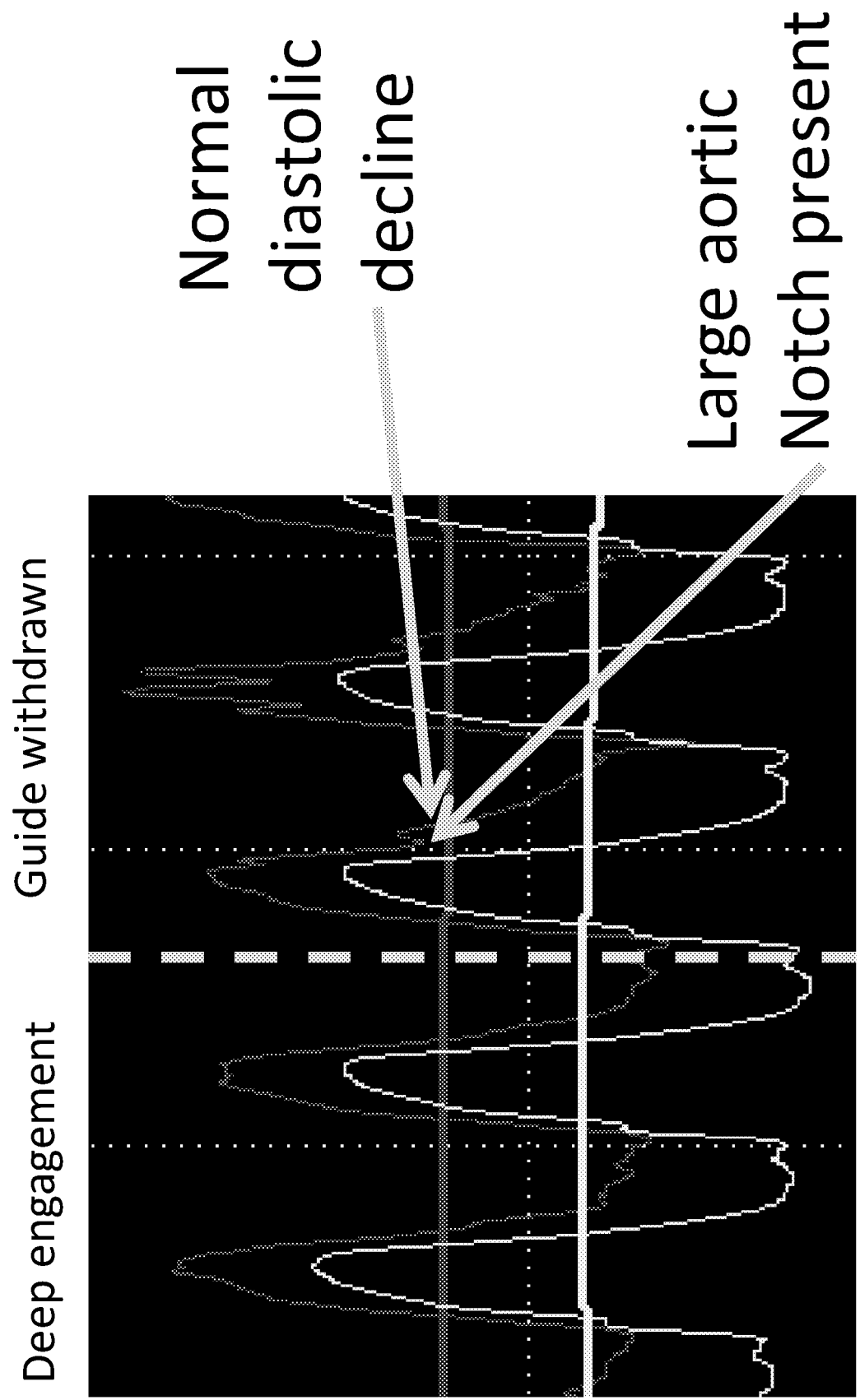
FIG. 12 is a continuation of the same waveform trace shown in FIG. 11.

FIG. 10 shows detection of damping artefact from the waveform and FIGS. 11 and 12 are further examples showing the waveforms associated with the above scenario where the catheter is withdrawn. FIGS. 11 and 12 are discussed in more detail below.

The control system 1 embodying the present invention directly reduces the time taken for a practitioner to be alerted to a patient safety concern and therefore reduces the time taken to initiate an intervention to prevent or alleviate a patient safety concern. In the above example, the control system embodying the present invention is aware of the patient safety concern in the space of, literally, one heart beat—a practitioner or experienced operator could well take longer to appreciate that the beats had transitioned from normal beats to damped beats.

In other examples, the control system 1 embodying the present invention can be monitoring pressure levels against the dataset 100 and the control system can give direct instructions to the medical practitioner to change the position of a stent from one location to another where the control system 1 identifies that the pressure is dropping and stent location would therefore be more beneficial.

In some embodiments, the control system requires a human user acknowledgement in response to a direct instruction or notification provided by the control system. The acknowledgement can be logged by the control system 1 as are other inputs and outputs from the control system to establish an audit trail and record of activity.

Examples of control systems embodying the present invention are illustrated in relation to a system for risk scoring for prediction of arterial disease and determining what, if any, form of intervention might be supported by the data. The system takes subject data 80 derived from the current patient 90 and tests for outcomes and interventions in the analyser 40. The present invention is not limited to the coronary field but has application in other medical fields such as aortic valve implantation—using TAVI valve under x-ray guidance; pacing wire implantation; stent insertion (coronary or peripheral); waveform analysis—damping; risk detection—peri-arrest situations; electrophysiolgy ablation treatments; and minimally invasive congenital or degenerative surgeries. Medical fields in which image data is consulted as part of the review, diagnosis or treatment are particularly well suited for use with the present invention.

In this example, a waveform detector 200 can take the output from various data sources 10 and operate on, for example: an image captured of a waveform; visual screen shots, raw digital data file formats, data from a data stream or data feed; or any other medium for representing a waveform. Using machine learning and object recognition, the waveform detector identifies, for example, a pressure waveform as an object usually from an image such as a trace. The recognised waveform is then available for extraction (decluttering and isolating the waveform data), categorisation (as a likely type of waveform: e.g. Pa or Pd waveform), normalisation (scaling to a standard template with at least a standard timescale and potentially amplitude for training a system on). The data from the waveform detector can be used to train the system 100 and provide data 20 to the system in a predetermined format.

The captured data 20 is provided from two main sources 10 but some data types can exist in or across both data types. It is advantageous to train, validate and operate the system using a broad spectrum of data including both sensed data 20 from multiple data sources 10 and study data 20 from a broad spectrum of relevant studies (and historical data).

One main data source 10 provides "sensed data" 20 such as captured or sensed data points, waveforms or images obtained from sensing equipment such as electrocardiograms, coronary pressure wires and transducers, angiograms, ultrasonic transducers, particularly coronary guidewire-mounted sensors to provide data on Fractional Flow Reserve—FFR, iFR (instant wave-free ratio (iFR) version of FFR), coronary flow reserve—CFR, the relationship between resting distal coronary pressure to aortic pressure ratio (Pd/Pa) and any other required metrics. Sensed data can also include data concerning: medical insurance profiles or social media feeds to give a perspective of a particular patient's lifestyle which may be an influence or risk factor.

The other main data source 10 provides what is termed "study data" 20 which can comprise historic data which includes patient risk factors, patient demographics and importantly such data often includes clinical outcomes and results which the system can utilise when training to assign risk probabilities associated with respective interventions and outcomes. The study data may also include sensed data or logs of historic sensed data and medical insurance profiles or social media feeds to populate the data set 100 with lifestyle information. Other examples of historic data include but are not limited to: Registry data; Actuarial risk tables; Clinical trial data; and/or Audit data.

Examples of sensed data sources include, but are not limited to: Pressure sensor guide wire (e.g. Volcano Verrata™ Pressure wire, Abbott PressureWire X™, Opens OptoWire™, ACIST Medical Systems. Navvus™ Microcatheter, or Philips CMET technology); Fluid filled catheter; Impedance flow sensor; Thermodilution flow sensor (Abbott PressureWire X™); Doppler Flow Wire (Volcano Combowire™); Ultrasound flow sensors (e.g. Transonic™) Non-invasive ultrasound measurements (Philips Echocardiogram machines); Social media inputs and feeds; Insurance profiles; Google trends data; Fluroscopic x-ray images; CT x-ray images; MRI images; and/or Non-invasive pressure based data (e.g. PulseCor™, or MobiloGraph™).

Data which can be captured or sensed includes, but is not limited to:
1. Aortic pressure waveforms
   a. Under hyperaemic or non resting conditions
   b. Under resting conditions
2. Pressure wire waveforms
   a. Under hyperaemic or non resting conditions
   b. Under resting conditions
3. Angiographic, CT or MRI imaging
4. Patient risk factors
   a. Smoking history
   b. Lipids
   c. Family history of IHD
   d. Previous IHD
   e. Diabetes mellitus
   f. Genetic profiling
5. Patient demographics
   a. Age
   b. Sex
   c. Race/ethnicity
   d. Height
   e. Weight
   f. Genome See FIG. 2 which shows the inputs (waveforms, Demographics, ECG & Angio, and RF profiling). Waveforms, ECG and Angio are all trained using AI to generate respective risk analysis/probability values. These are then used in a weighted model alongside other variables (Demographics) and (RF profiling) to produce the risk analysis which can be output as a predictive mode (Likelihood of Diffuse or likelihood of Focal, risk associated with "Treat" or risk associated with "no-treat"). The accuracy of the system depends on the training sets, node values and weightings between the different inputs.

In the analyser 40, each of these data sources are used in consort, to build up a probability matrix trained to deliver a risk analysis of various "treat"/"no treat" options based on trained data. The system delivers a risk analysis of what the risk is if the patient is treated with an option or the risk if the patient is not treated with a treatment option. Importantly, the risk analysis is delivered by the system which has been trained to take into account not just the input data but the trained data which can be a very broad spectrum of data so that the delivered risk analysis takes into account (i.e. has been trained on) not just the input data, in this case pressure waveforms, but also other data including both study data and other captured or sensed data. The delivered risk analysis is informed by the broad spectrum of data on which the system has been trained and operated. A fully experienced physician attempting to arrive at a decision on whether to treat or not treat in a particular manner would not have access to the broad spectrum of data on which the system has been trained so the risk analysis delivered by the system is a useful tool for a physician.

Examples of "treat"/"no treat" options include:
1) Treat/no treat of an arterial stenosis based on ischaemic prediction
2) Treat/no treat of an arterial stenosis based on mortality/morbidity prediction The system is also trained to deliver an identification of a diffuse or a focal disease.

Each input is trained against known treatment guidance: Fractional Flow Reserve—FFR, iFR (instant wave-free ratio (iFR) version of FFR), coronary flow reserve—CFR, the relationship between resting distal coronary pressure to aortic pressure ratio (Pd/Pa) etc., and known clinical outcomes (death, MI, revascularisation). From these, probability node values are determined in the analyser 40 linking each input to clinical outcomes and/or interventions so that the system is trained to deliver a risk factor or probability associated with a "treat" or "no treat" intervention.

Flow waveforms carry a significant amount of information which may not easily be available to the pressure waveforms. For instances, due to the Bernoulli effect even a mild stenosis can look severe using pressure waveforms when the flow is normal. When flow is not measured it is not possible to know whether a stenosis is significant or if the flow was just very high. By training pressure waveforms against known flow waveforms and their outcomes it is possible to derive more of the benefits of measuring flow from the pressure waveforms themselves.

Figure 13:
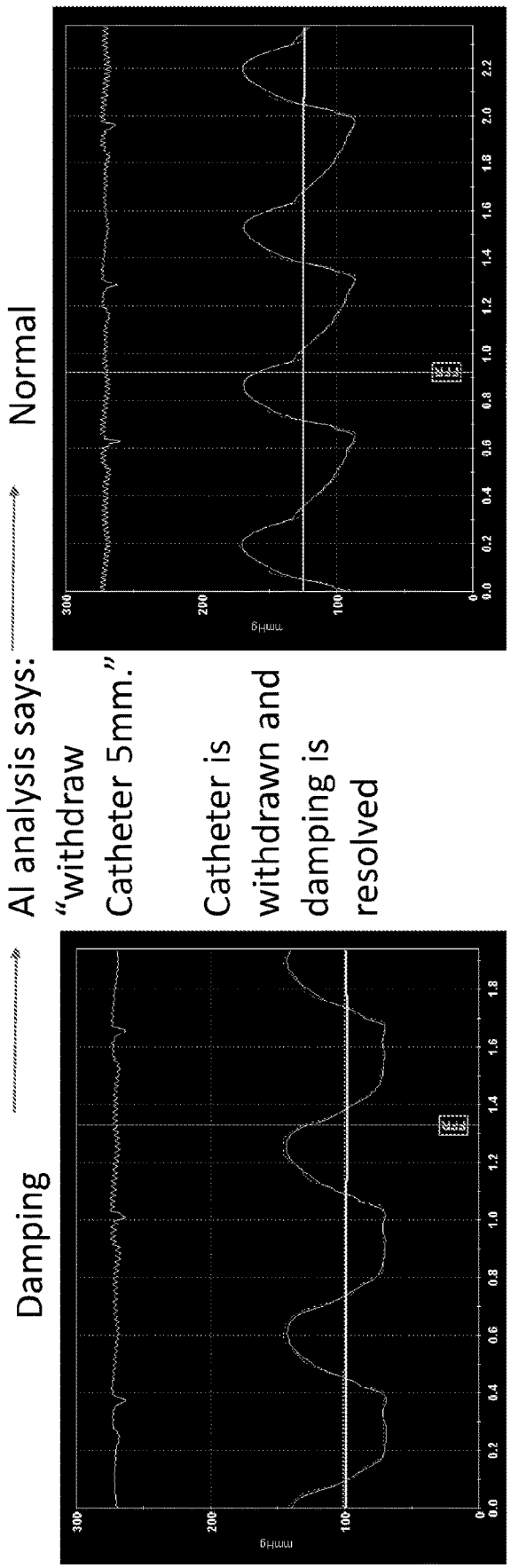
FIG. 13 is a schematic representation of the analyser identifying damping effects and specifying an intervention which is to withdraw a guiding catheter by a predetermined amount to remedy the damping effects.

For example, see FIG. 13 which takes the original sensed data and inputs that to the data set for analysis by the analyser 40. The analyser 40 determines from the data set 100 that there is a high probability that there is damping present in the system and the "treat" intervention recommended is to withdraw the catheter by 5 mm.

Figure 14:
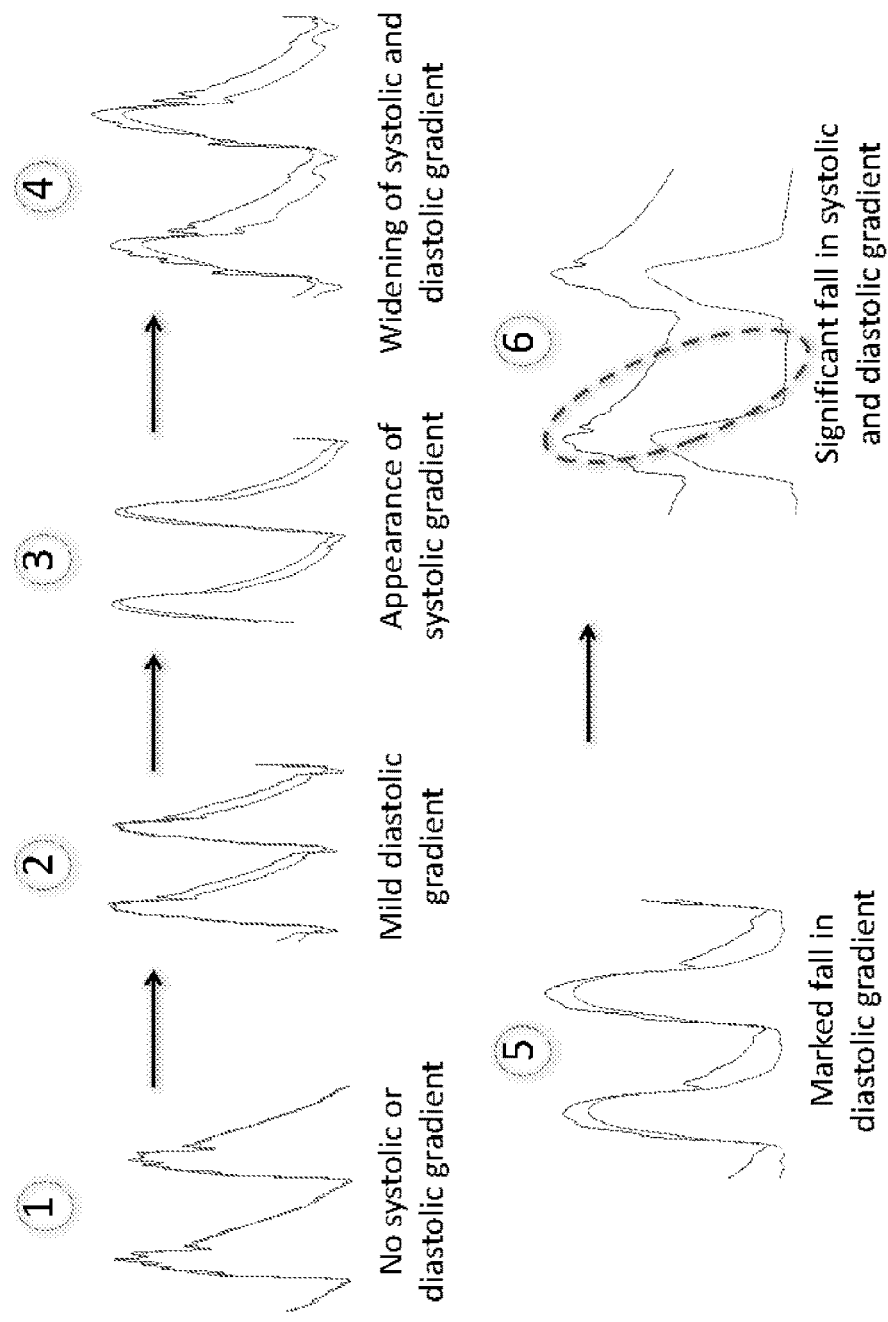
FIG. 14 is a selection of pressure waveform traces which have a trace indicative of respective characteristics associated with that waveform to enable training for recognition of said characteristics.

FIG. 14 shows various waveforms comprising sensed data which the system trains to correlate the characteristics associated with the respective waveforms.

Figure 19:
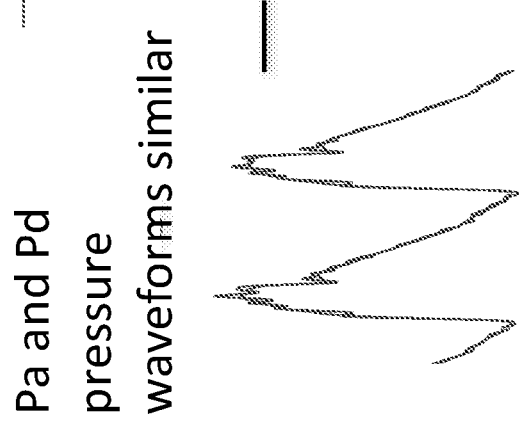
FIG. 19 illustrates a pressure waveform as input to the analyser embodying the present invention and a treatment indicator.
Figure 20:
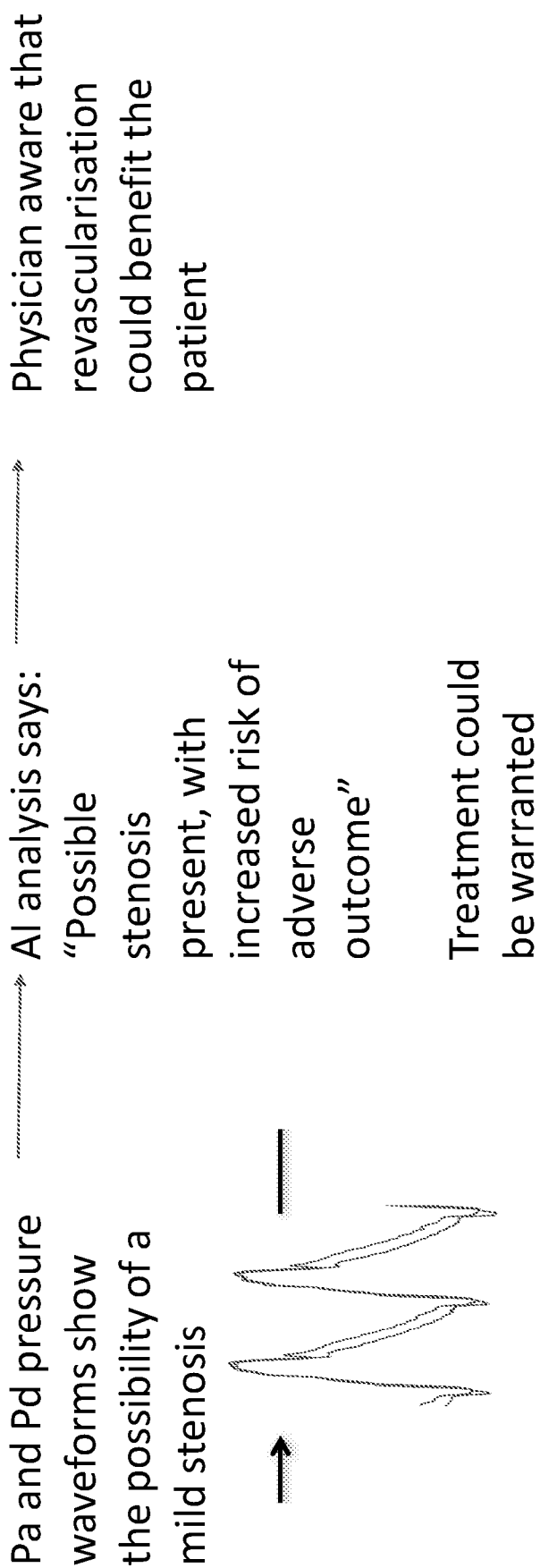
FIG. 20 illustrates a further pressure waveform as input to the analyser embodying the present invention and a treatment indicator.
Figure 21:
FIG. 21 illustrates another pressure waveform as input to the analyser embodying the present invention and a treatment indicator.

FIGS. 19 to 21 illustrate the sensed data comprising a pressure waveform showing Pa and Pd pressure which is taken as the data input 00 from the patient. The analyser 40 delivers a risk analysis or probability of an adverse outcome and indicates whether "treat" or "no treat" might be beneficial. In these cases, the significance of the potential stenosis is rated by the analyser 40 and an associated probability is associated with the respective outcome and treatment indication.

Figure 2:
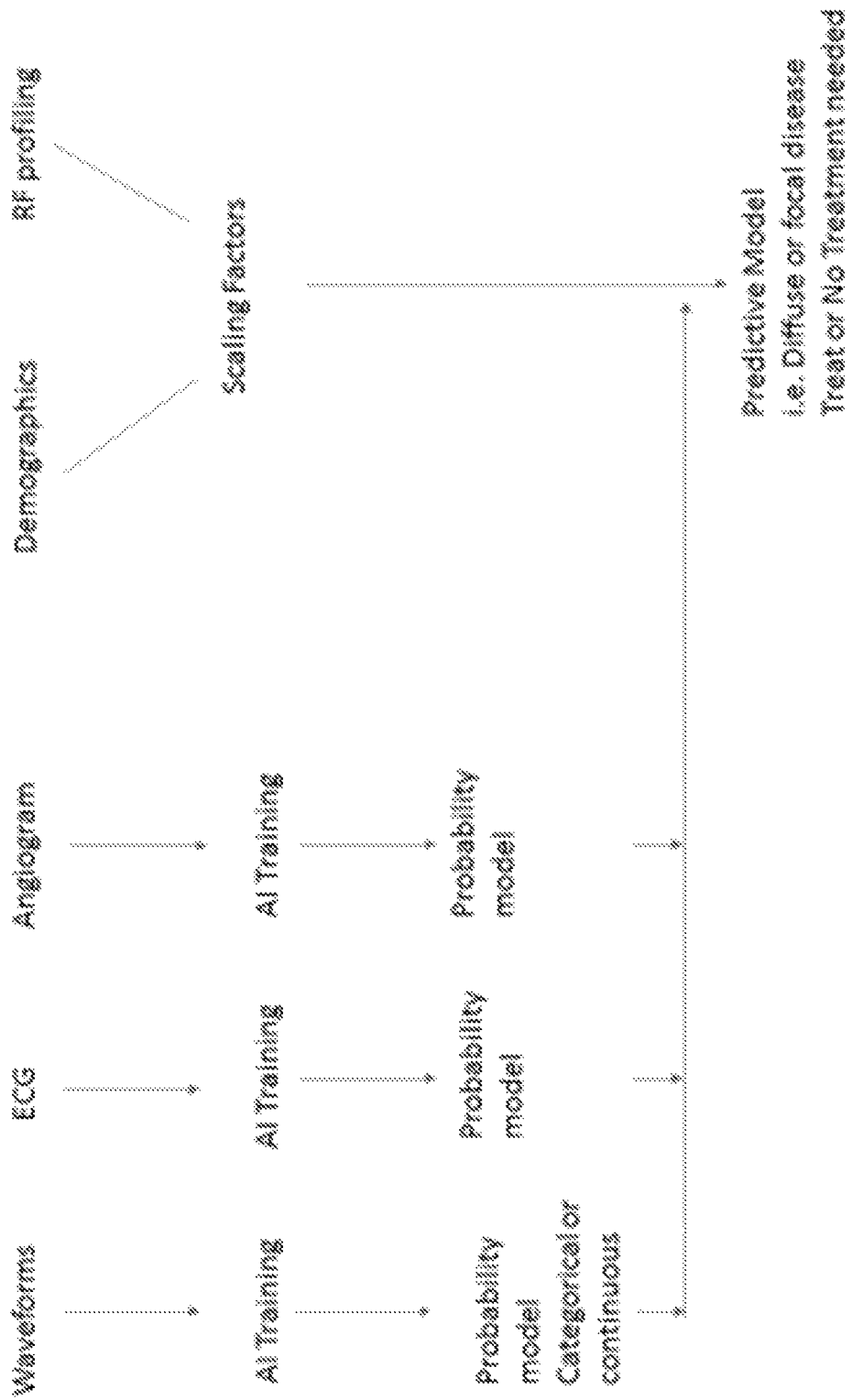
FIG. 2 is a detail showing one potential configuration for an analyser for use with the present invention.
Figure 3:
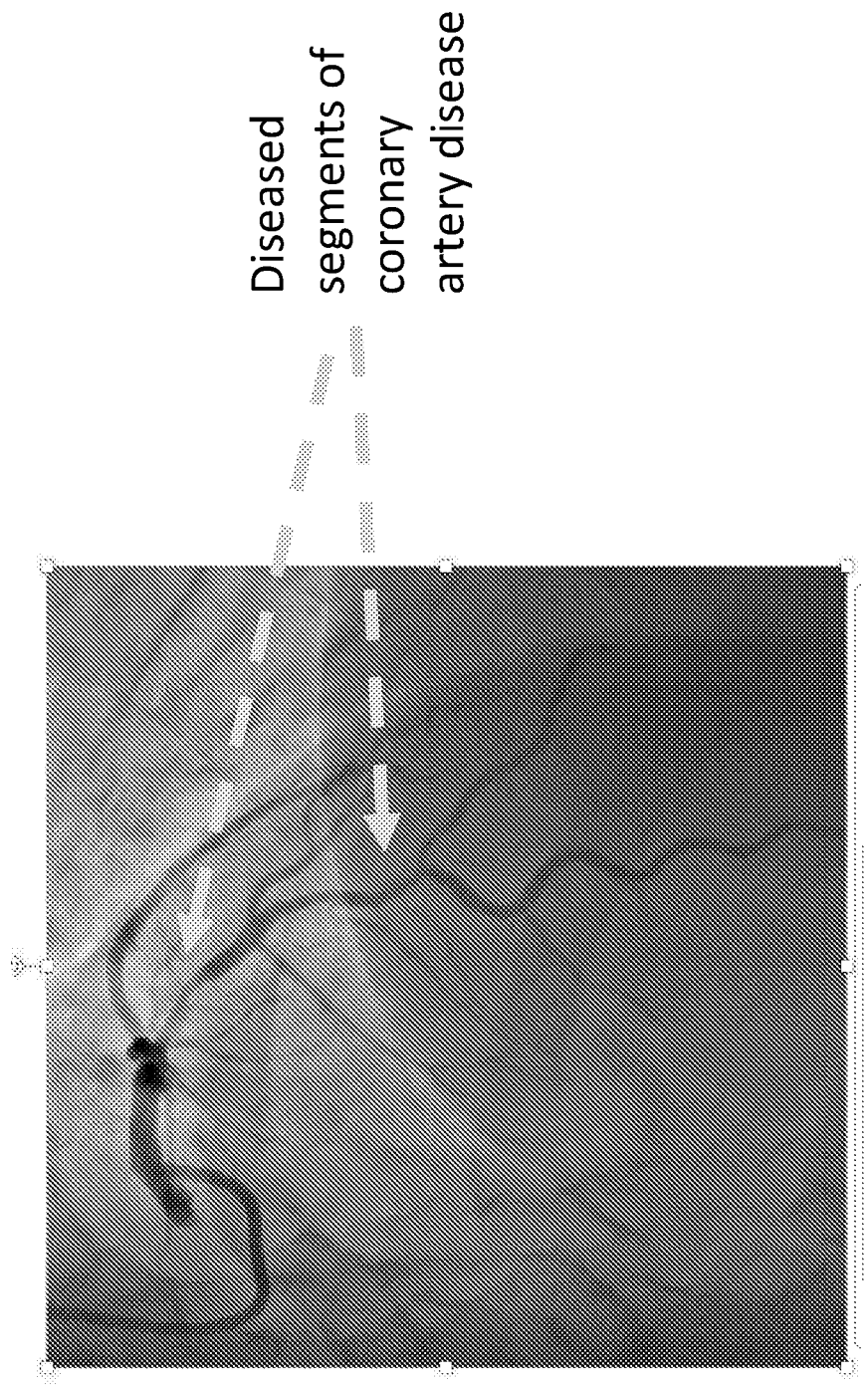
FIG. 3 is an image showing visible coronary artery disease.
Figure 4:
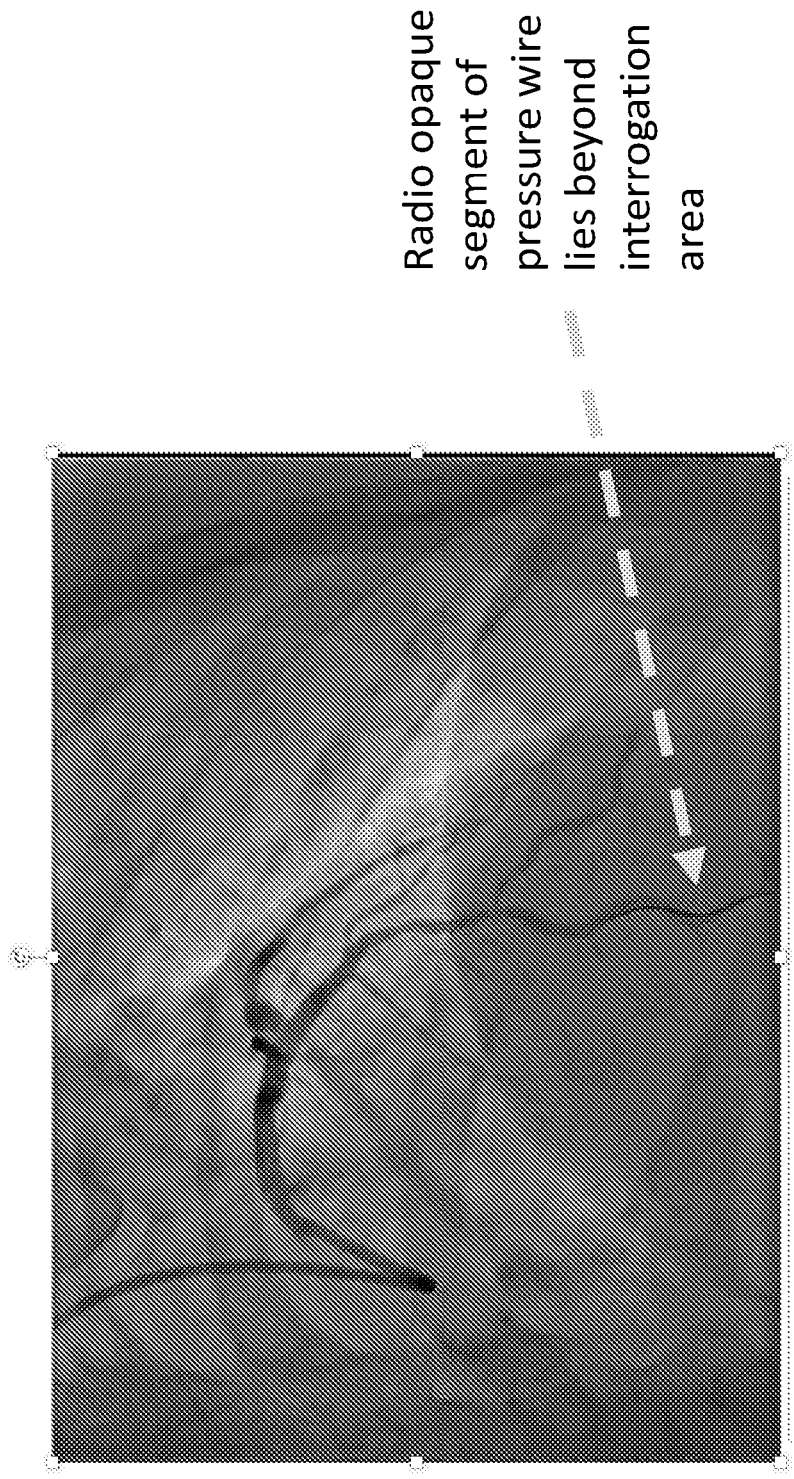
FIG. 4 is the image of FIG. 3 and a pressure wire for monitoring pressure in the arteries being pulled back to take pressure readings.
Figure 5:
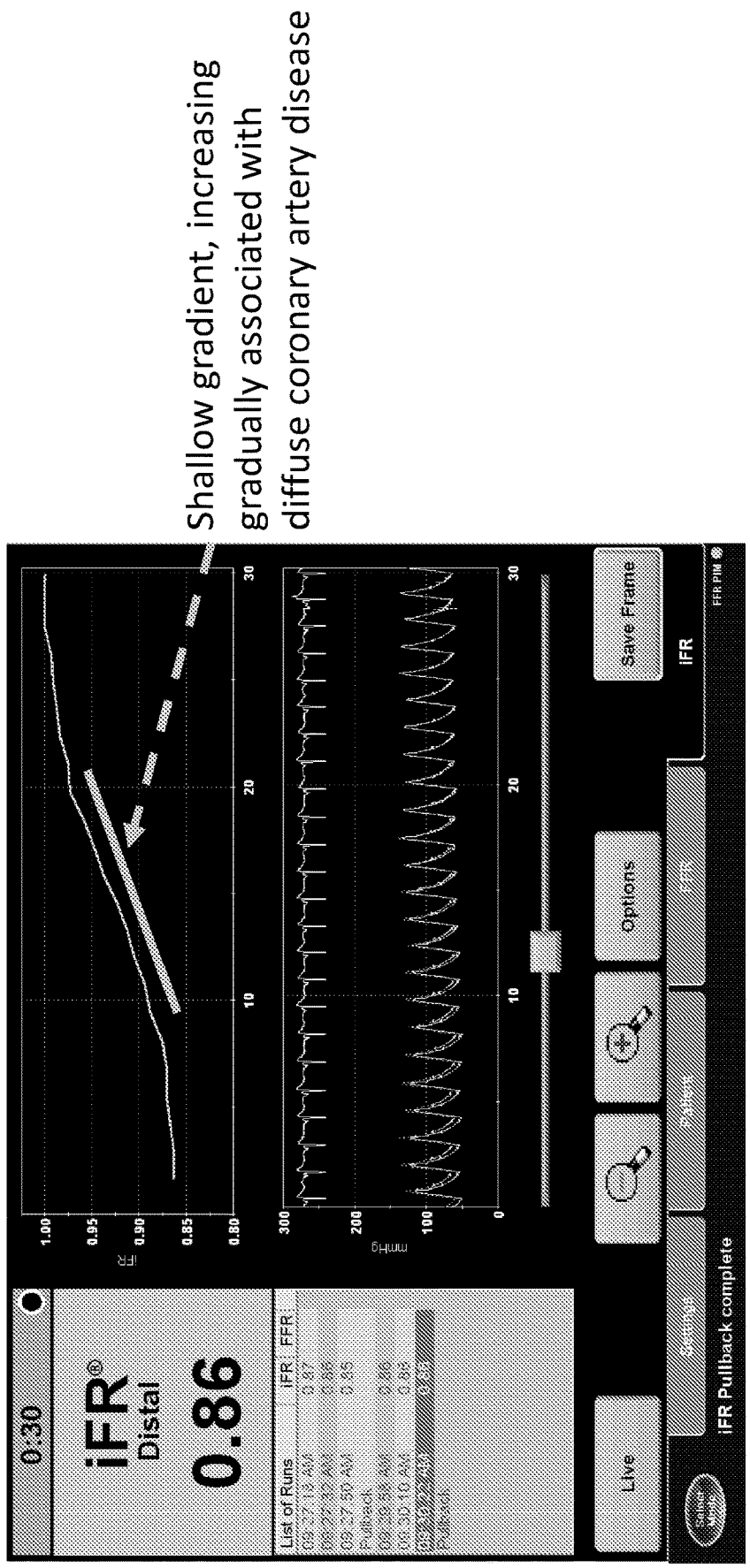
FIG. 5 is an example of a pressure trace from a pressure wire being pulled back through a subject artery recording the distal pressure along the length of the artery, the form of the trace is indicative of diffuse coronary artery disease.
Figure 6:
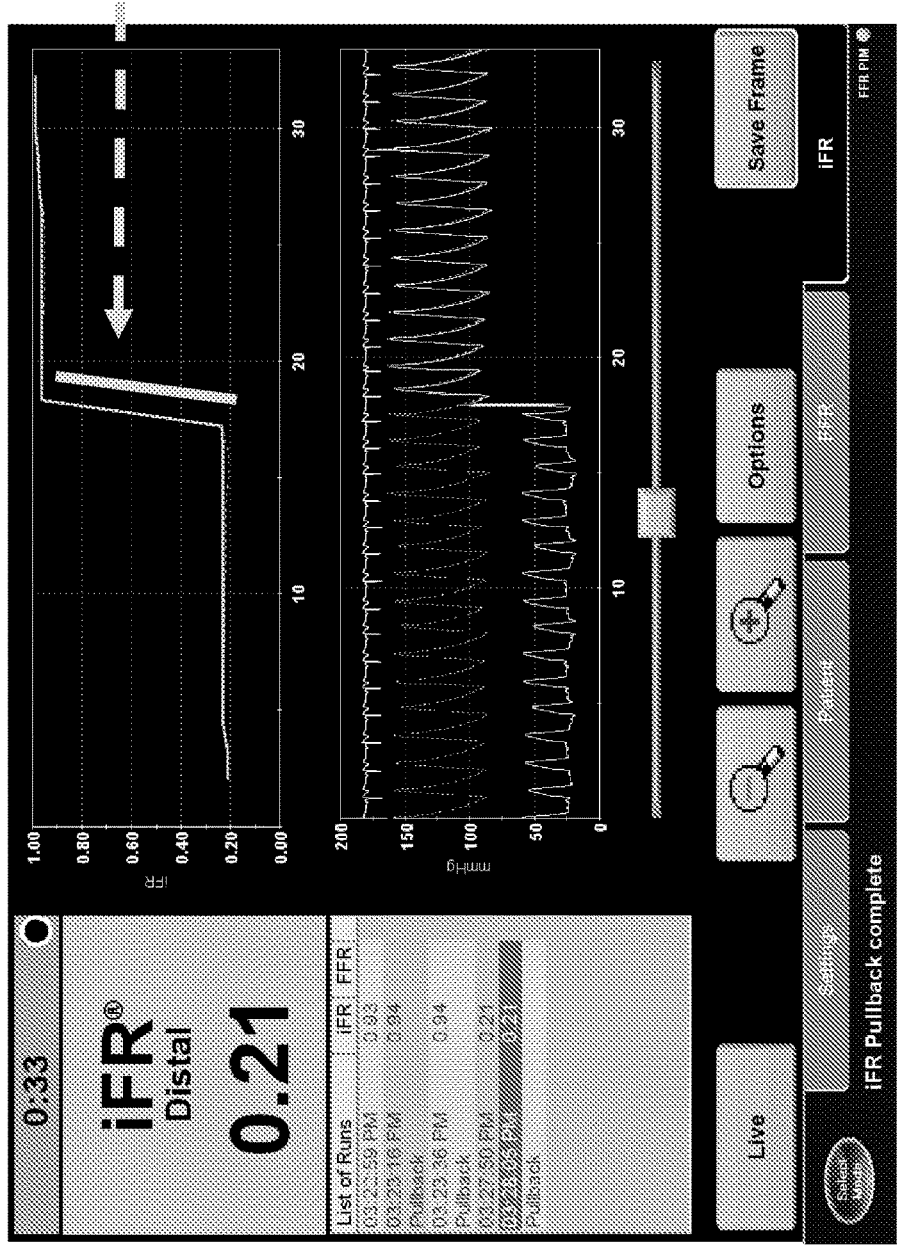
FIG. 6 is an example of a pressure trace from a pressure wire being pulled back through a subject artery recording the distal pressure along the length of the artery, the form of the trace is indicative of focal coronary artery disease.
Figure 7:
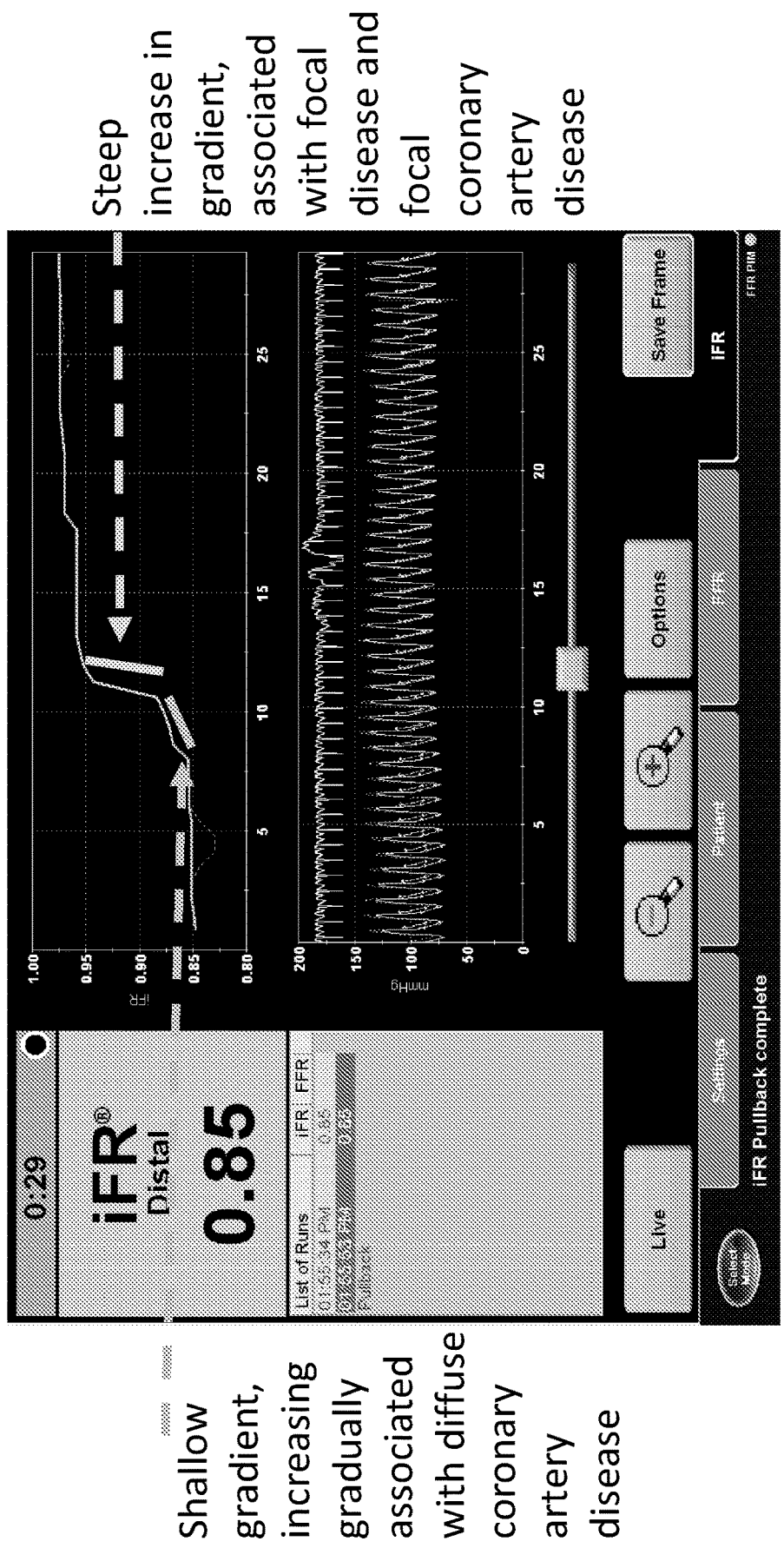
FIG. 7 is an example of a pressure trace from a pressure wire being pulled back through a subject artery recording the distal pressure along the length of the artery, the form of the trace is indicative of a mixture of focal and diffuse coronary artery disease.
Figure 8:
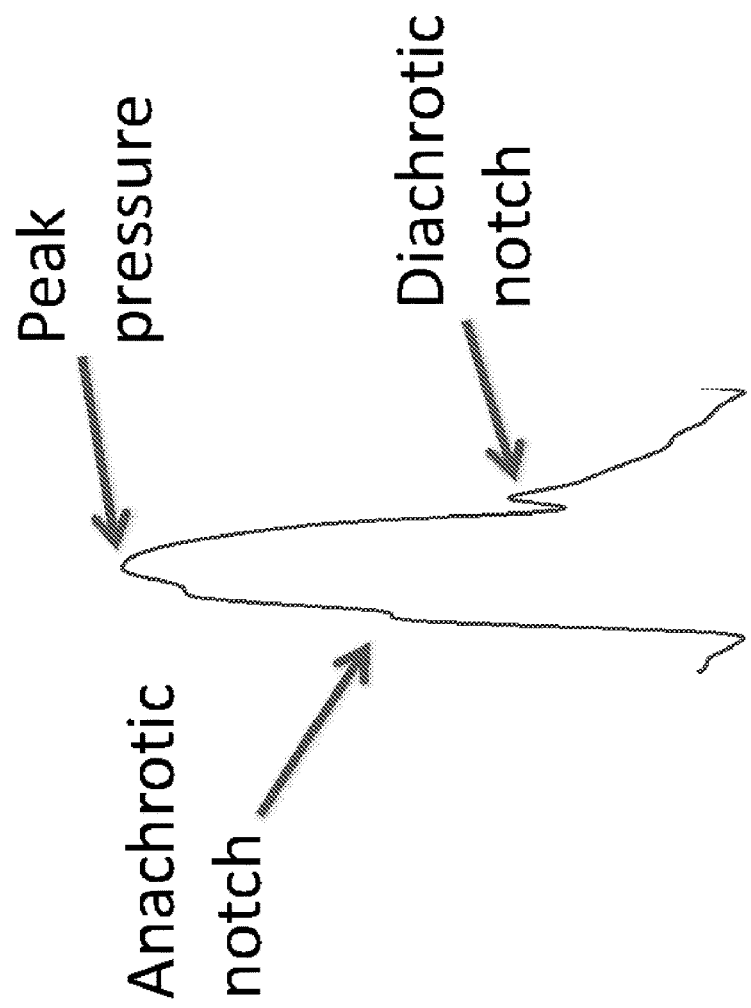
FIG. 8 is a schematic representation of the features of a "normal"/healthy pressure waveform.
Figure 9:
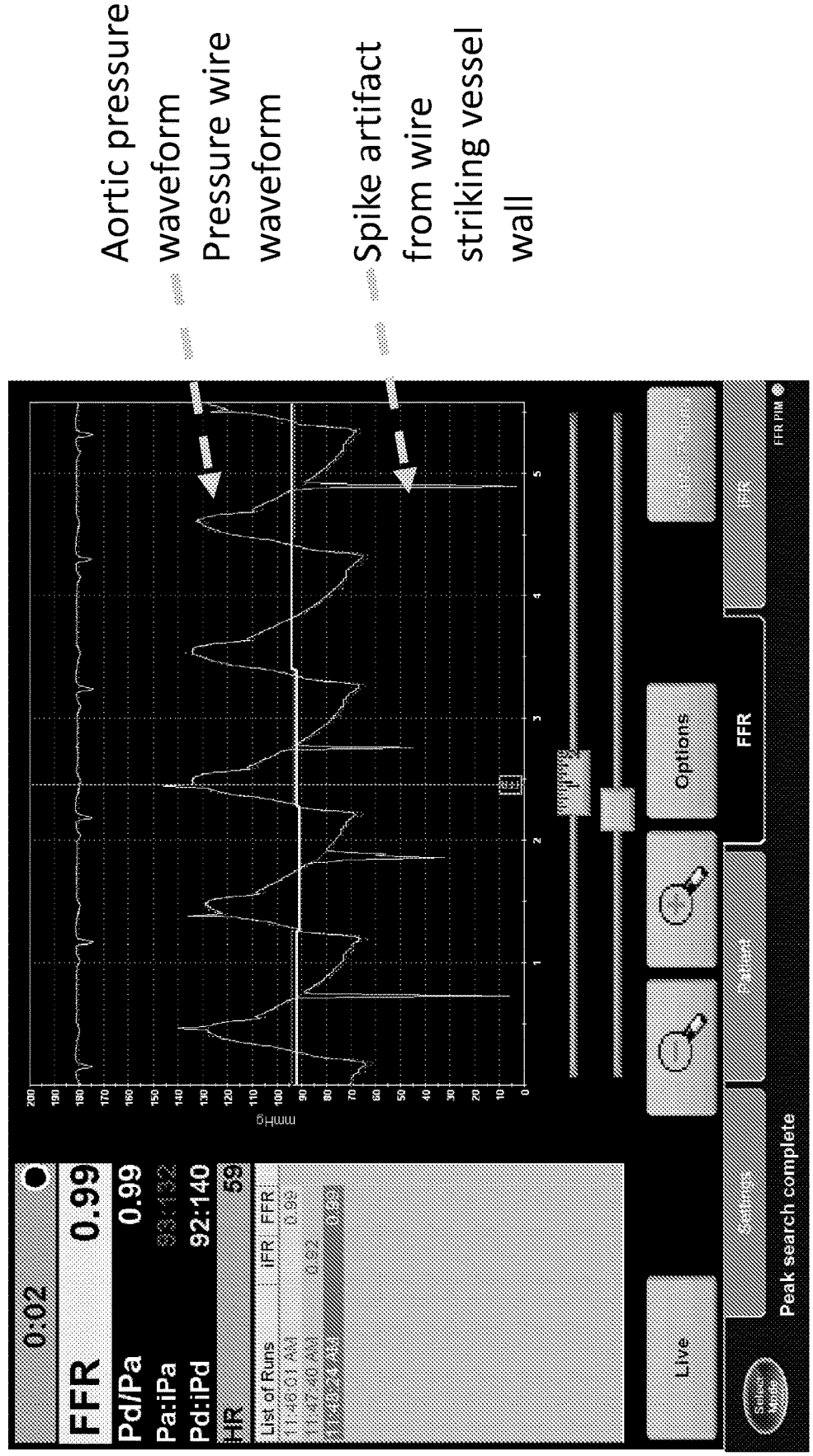
FIG. 9 is a trace of a series of pressure waveforms showing spike artefacts.

Referring to FIG. 2, the analyser 40 is trained using the above captured data. The analyser develops a unique scaling risk factor modifier as follows.

The analyser 40 uses a training algorithm for providing a risk analysis for "treat"/"no treat". Examples of "treat"/"no treat" options include:
1) Treat/no treat of an arterial stenosis based on ischaemic prediction; and/or
2) Treat/no treat of an arterial stenosis based on mortality/morbidity prediction.

In this example, the analyser utilises the open-source Keras™ machine learning library, running on top of the Google Tensorflow™ backend. The Python™ programming language was used. The neural network used for estimation from traces such as pressure waveforms is a long short-term memory (LSTM) recurrent neural network with a single output neuron. Training was performed using the Adamax optimiser. The neural network used for classifying pullback traces as diffuse or focal took the form of a convolutional neural network using the Google's GoogLeNet Inception V3 architecture and a single output neuron acting as a binary classifier. Training was performed using the Adam optimiser.

This produces effective results for this example and analogous examples particularly for analysing medical or physiological data in the form of images such as analysing waveform-like data or traces and CT, MRI, X-ray and other physiological or medical image data.

In another example, the neural network is used for classifying pullback traces as diffuse or focal, In this example, the system is trained to deliver an identification of a diffuse or a focal disease. The analyser 40 uses a convolutional neural network using GoogLeNet Inception V3 architecture and a single output neuron acting as a binary classifier.

| FIG. | Input data 00 | Stenosis detected by analyser 40? | Adverse outcome risk analysis delivered by analyser 40 | Treatment or intervention indicated by analyser 40 |
|---|---|---|---|---|
| 19 | Pa and Pd Pressure waveform | No stenosis | Low risk of adverse outcome | No treat |
| 20 | Pa and Pd Pressure waveform | Potential stenosis | Increased risk of adverse outcome | Could treat - revascularisation |
| 21 | Pa and Pd Pressure waveform | Significant stenosis | High risk of adverse outcome | Treat - revascularisation |

Figure 15:
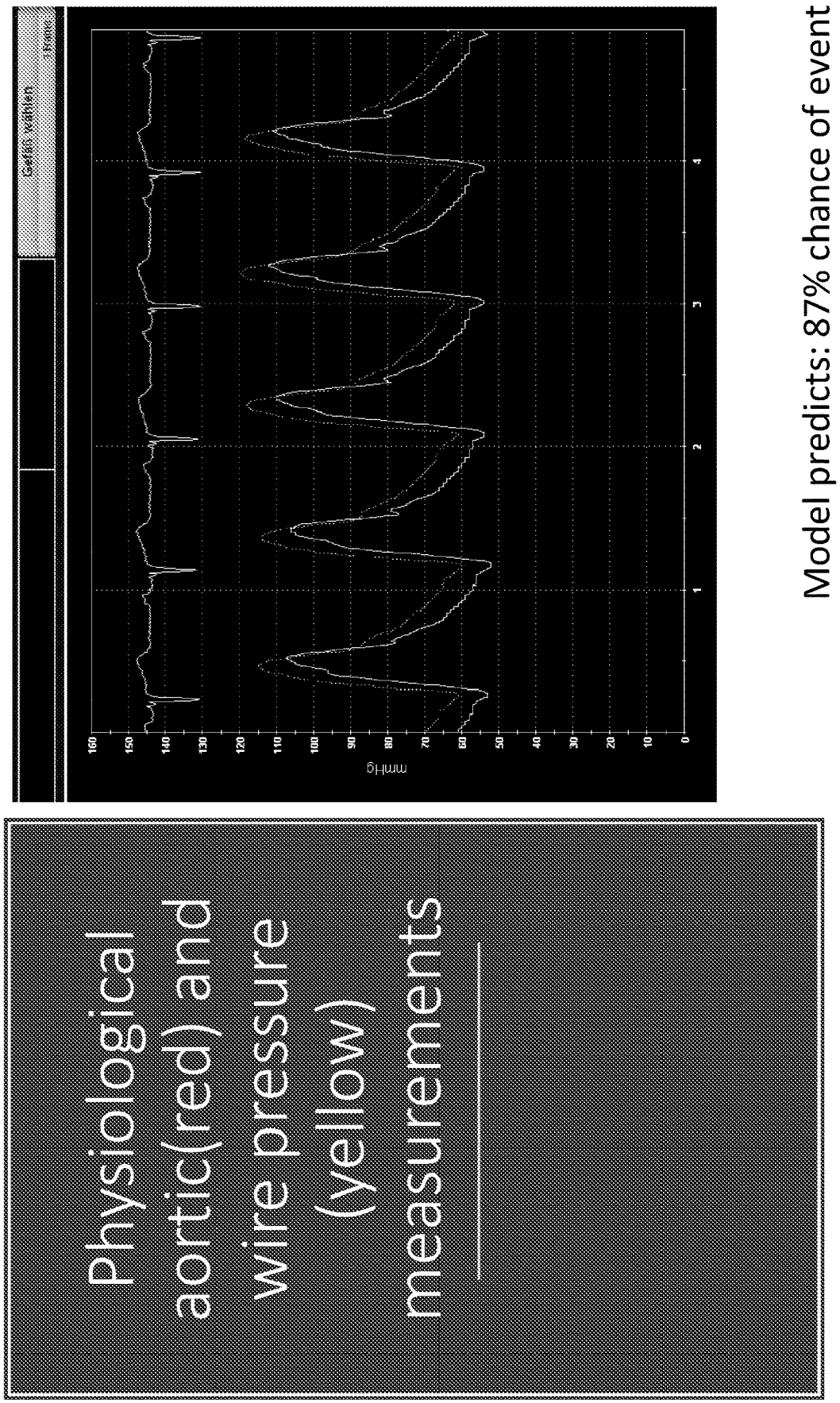
FIG. 15 is a series of pressure waveforms which the analyser embodying the present invention has reviewed to determine the probability of an outcome or event.
Figure 16:
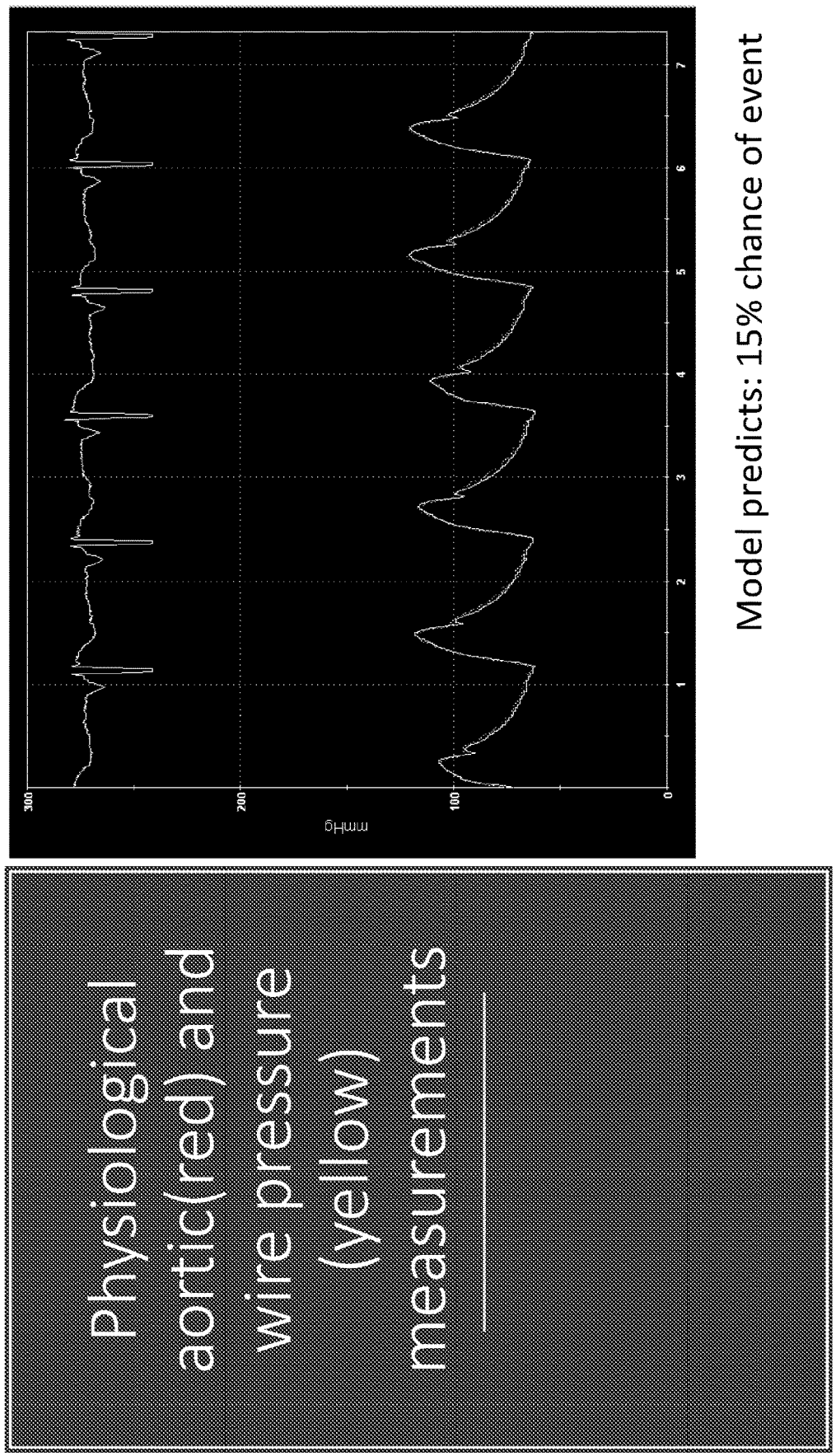
FIG. 16 is another series of pressure waveforms which the analyser embodying the present invention has reviewed to determine the probability of an outcome or event.
Figure 17:
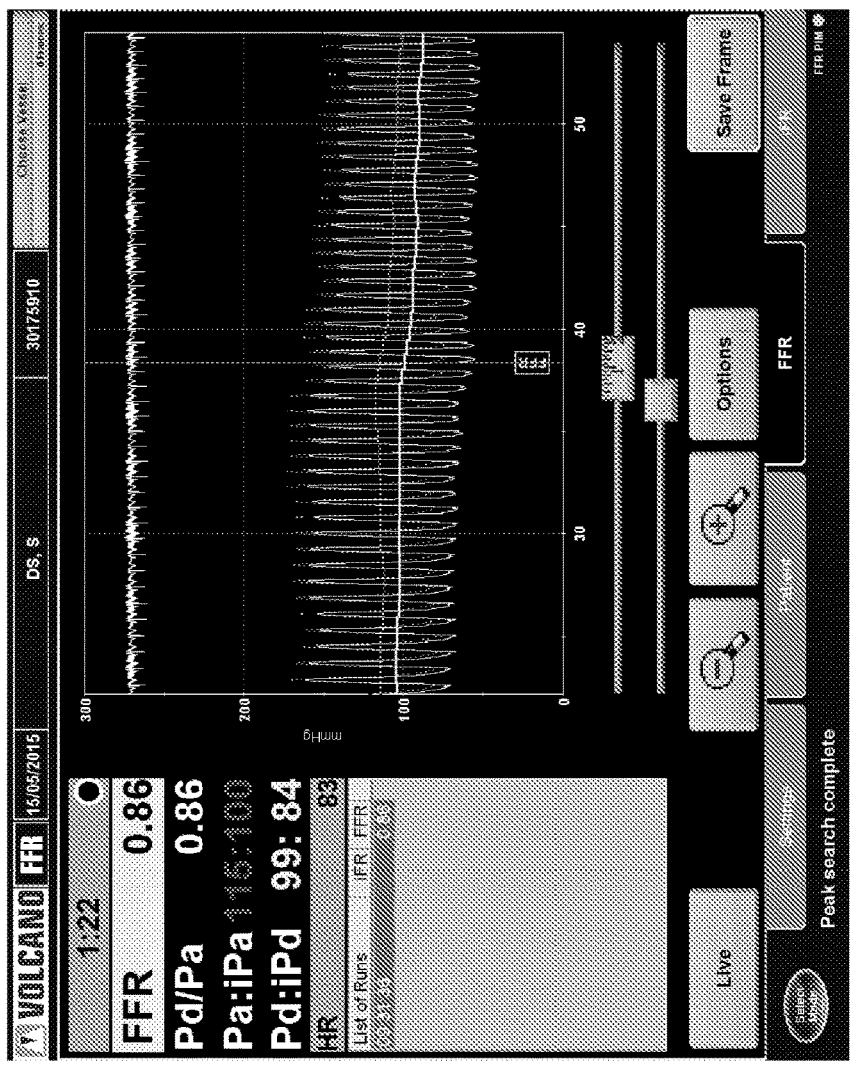
FIG. 17 is a further series of pressure waveforms which the analyser embodying the present invention has reviewed to determine the probability of an outcome or event.
Figure 17:
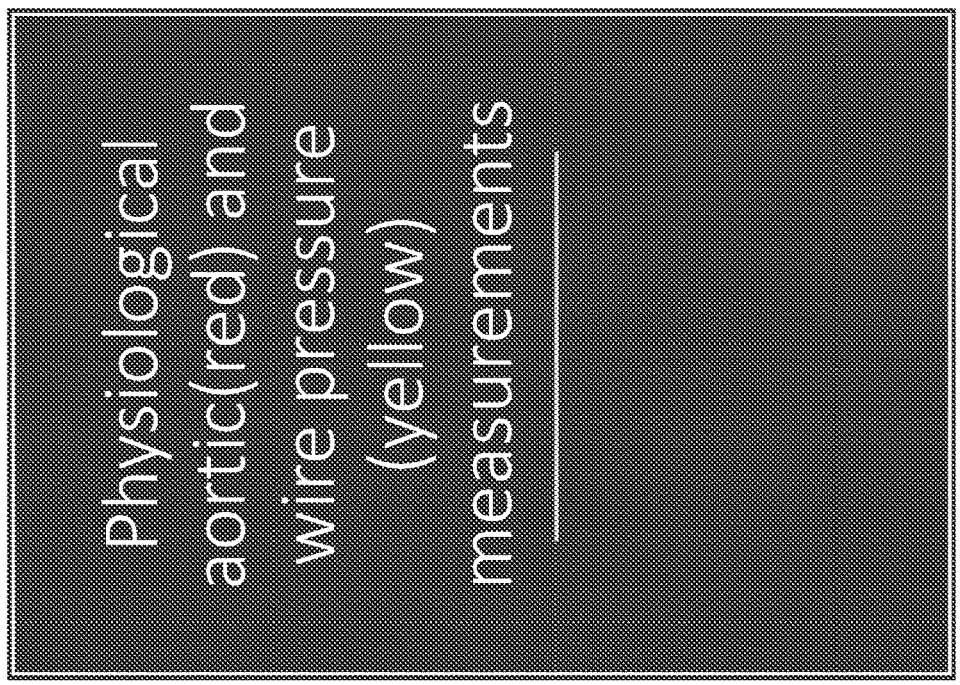

Other examples of the analyser reviewing waveform sensed data are shown in FIGS. 15 to 17 where the analyser associates a risk factor with a particular outcome.

The analyser 40 is operable to analyse the subject data 00 with respect to the data set 100 from the at least one data source 10 and output an associated probability 50/60 for each of one or more outcomes 30, wherein the associated probability is affected by an intervention.

Probability node values from each input are then run in a large matrix, where each value is iterated by further input from the fields. In this way, a series of probability node values are determined for each of the inputs when used individually or when used in consort with other inputs.

These node values are then used to determine the need for treatment, the probability of significant mortality and morbidity, risk analysis and the ability to discriminate between focal and diffuse disease. Decision-making is then performed according to this guidance which comprises assigning a probability to each outcome or potential intervention so as to then make a determination, potentially in consultation with a health professional or to better inform the practicing health professional about what outcomes or interventions to consider.

Training was performed using the Adam optimiser. This produces effective results for this example and analogous examples particularly for analysing medical or physiological data in the form of images such as analysing waveform-like data or traces and CT, MRI, X-ray and other physiological or medical image data.

Figure 23:
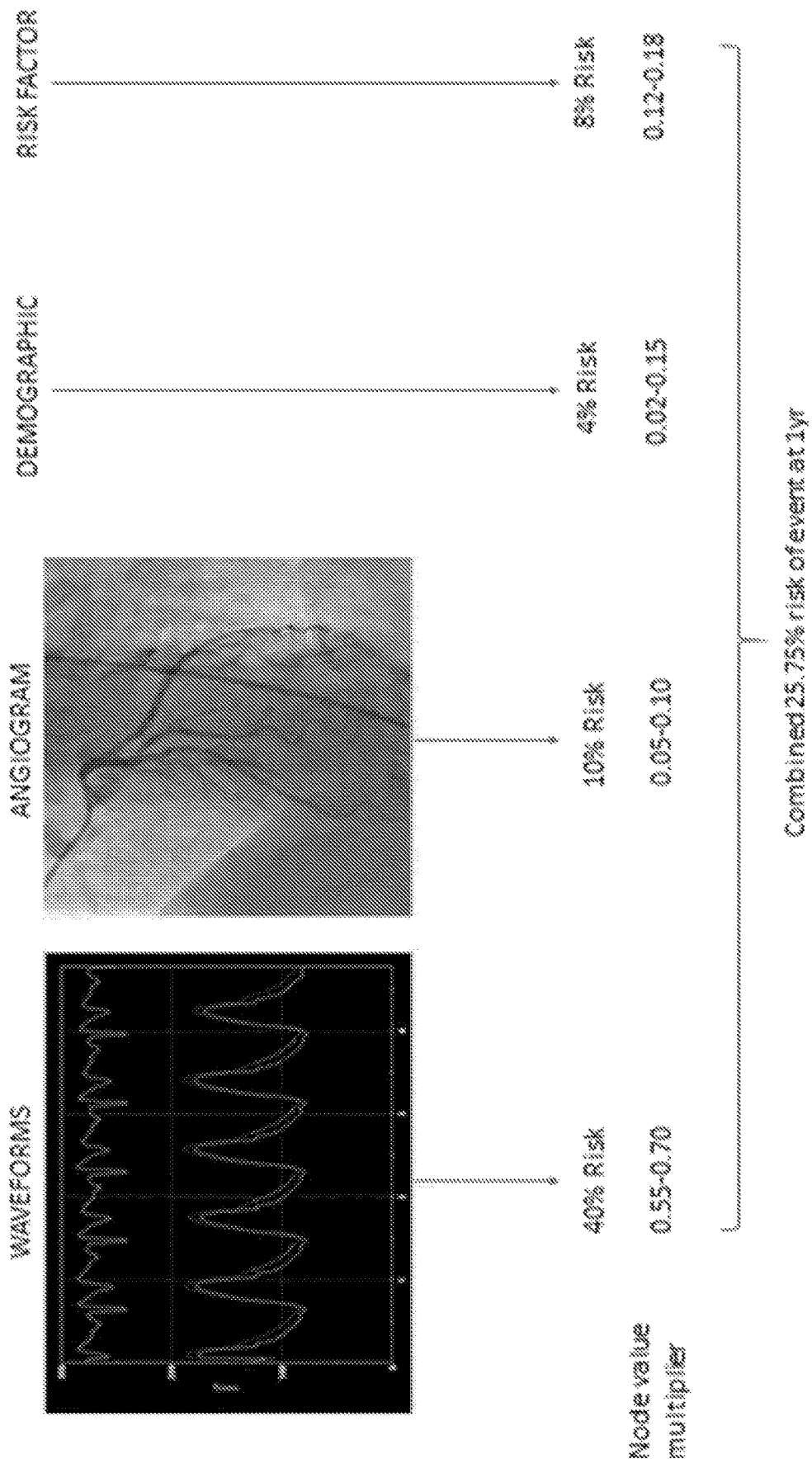
FIG. 23 illustrates the weighted combination of the various analyses employed in embodiments of the present invention.

The captured data variables shown in FIG. 2 (physiology waveforms, ECG, angiograms, demographics and risk factor profiling) are individual variables which are weighted to vary how much of a contribution they each make to the overall diagnosis/outcome suggested. In this way, the system further refines the probability of a clinical event occurring, beyond what could be achieved from any one of the single inputs (specifically here thinking of pressure waveform) alone. Embodiments of the claimed invention are an effective tool which improves upon an index-based risk analysis as previously conducted. So, in an example it could be that a 60% probability of an event derived from the waveform data alone could get a significant uplift of say an additional 10% from the RF profiling, but a decrease of 3% from the demographic profiling. In this way the pressure waveforms ability to predict clinical events are modulated or tuned according to the other variables in the model. FIG. 23 illustrates another example where pressure measurement, following waveform analysis identifies a 40% risk of an event—that node has a weighting of 0.55 to 0.70. The angiogram image is analysed by the system and delivers a 10% risk of an event—that node has a weighting of 0.05 to 0.10. The other factors in this example are the demographics and risk factors which respectively identify a 4% and 8% risk of an event—those nodes have respective weighting ranges of 0.02 to 0.15 and 0.12 to 0.18.

The output of all the nodes is combined/multiplied to deliver a combined risk probability of 25.75% of an event within one year.

The weightings (ranges of weightings) have been tuned for the present medical application.

FIGS. 3 to 14 show various traces and waveforms as images which are entered into the system and used to train the analyser 40 based on the characteristics of each of the images and the ancillary data associated with the patient from which the image data was recovered. The ancillary data may be patient information such as age, sex, indications, prior history, demographics, prescription history, corresponding ECG or angiogram readings for the same patient. All the image data and ancillary data populates the dataset 100 and is used to train the analyser so that when new data is received from a patient 90, that new data 10 can be provided as subject data 80 to the data set 100 and compared against the data set 100 and analysed by the analyser 40 to output one or more likely outcomes, each with an associated probability. Referring to FIGS. 15 to 17, the waveforms are reviewed by the analyser 40 and assessed with a probability of an event arising. The event may be a cardiac event or a recommendation to deploy a particular intervention.

For example, FIG. 11 is a pressure waveform trace having particular characteristics—the first two beats (left to right) show significant damping of the aortic (red waveform). This causes the beat to appear abnormal as highlighted by the illustration (Ventricular aortic morphology), and can lead to an inaccurate measurement which uses the ration of the Pa (red) and Pd (yellow lines). FIG. 12 is a continuation of the same waveform trace shown in FIG. 11 but in beats three-four, the catheter has now been withdrawn to remove damping. The segment of the waveform which had been depressed now has a normal appearance ("Normal diastolic decline"), additionally the aortic notch is now visible ("large aortic notch present). This means that the measurement will no longer be affected by artefact, and a proper measurement is made. The system is able to detect the apparently abnormal waveform shown in FIG. 11 and advise that it is providing inaccurate or not representative data and recommend a probability that a solution will improve the readings. In this case, the system recommends the withdrawal of the catheter to allow proper representative measurements to be made.

Figure 18:
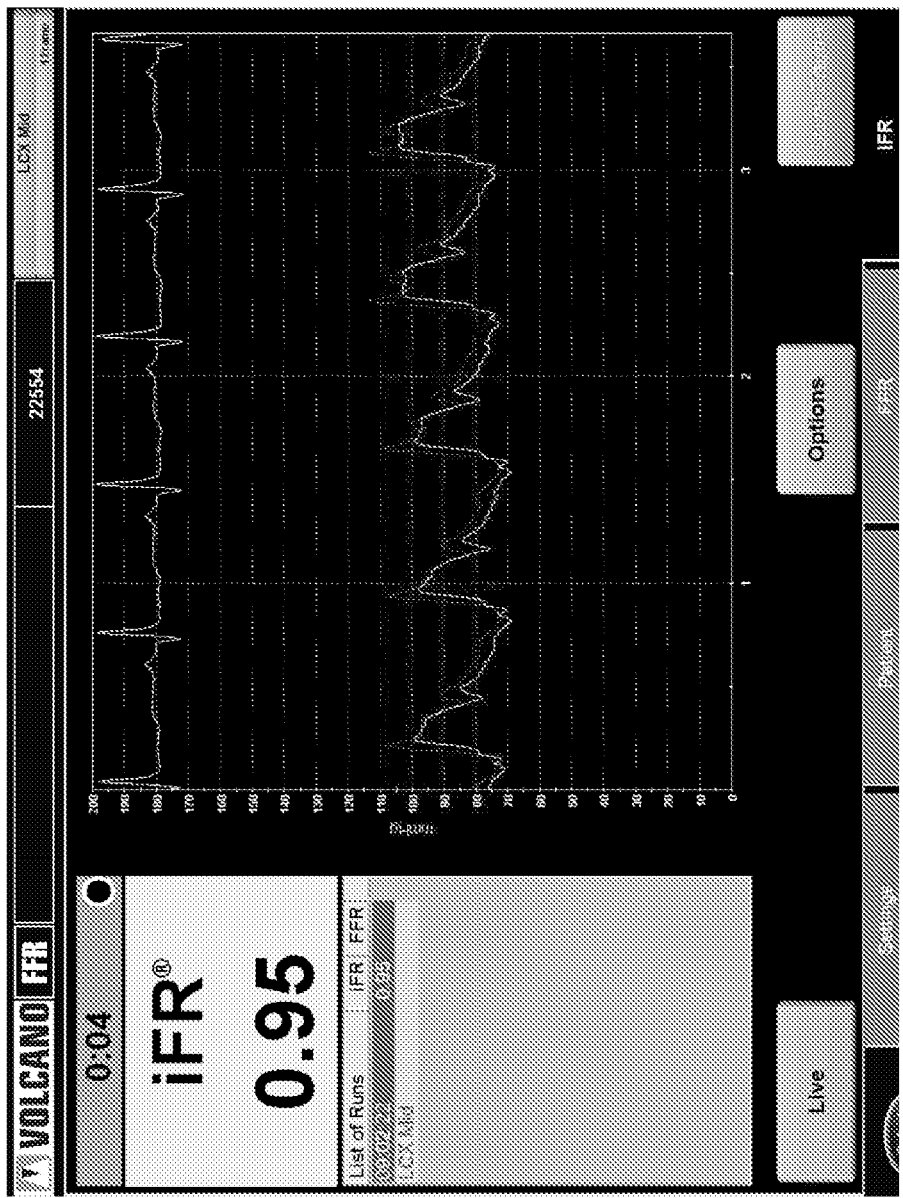
FIG. 18 is a series of pressure waveforms which the analyser embodying the present invention has reviewed to determine a potential outcome.

FIG. 18 is an example of a waveform shape which typically will be associated with an increased risk of vascular disease. The machine learning process learns from the training data set to associate this waveform shape with a higher risk patient, by extracting various features from the waveform.

The outcomes may be a diagnosis of a condition and/or a suggested intervention. In more detail, the output of the analyser 40 is passed to the risk analysis assessment module 50 to provide a health professional with a tailored risk analysis and/or is passed to the action and alert management module 60 which can provide feedback to the health professional concerning what action might be recommended or what alerts should be flagged for further attention.

If an intervention is suggested by the system, then the intervention allocation module 70 can automate the intervention or provide guidelines or instructions to effect the intervention. When the intervention is effected or after a predetermined time period for the intervention to have had an effect, the data 10 for the patient 90 can be taken again and the feedback loop closed to re-evaluate the patient's condition.

The analyser 40 is continually iterated by using new input and outcomes data to train the model, with the probability node values getting constantly modulated by comparing the analyser's diagnostics scoring against, mortality and morbidity records for that patient. In this way the accuracy of the analyser 40 continues to improve, and becomes more accurate in the determination and prediction of clinical outcomes and suggested interventions.

The probability node ranges are as follows for each of the inputs:

Aortic pressure waveforms vs need for treatment: n1, n2 etc.

Pressure wire waveforms signal vs need for treatment: n1, n2 etc.

Angiographic or CT imaging vs the need for treatment: n1, n2 etc.

Patient risk factors vs the need for treatment: n1, n2 etc.

Patient demographics vs the need for treatment: n1, n2 etc.

Figure 22:
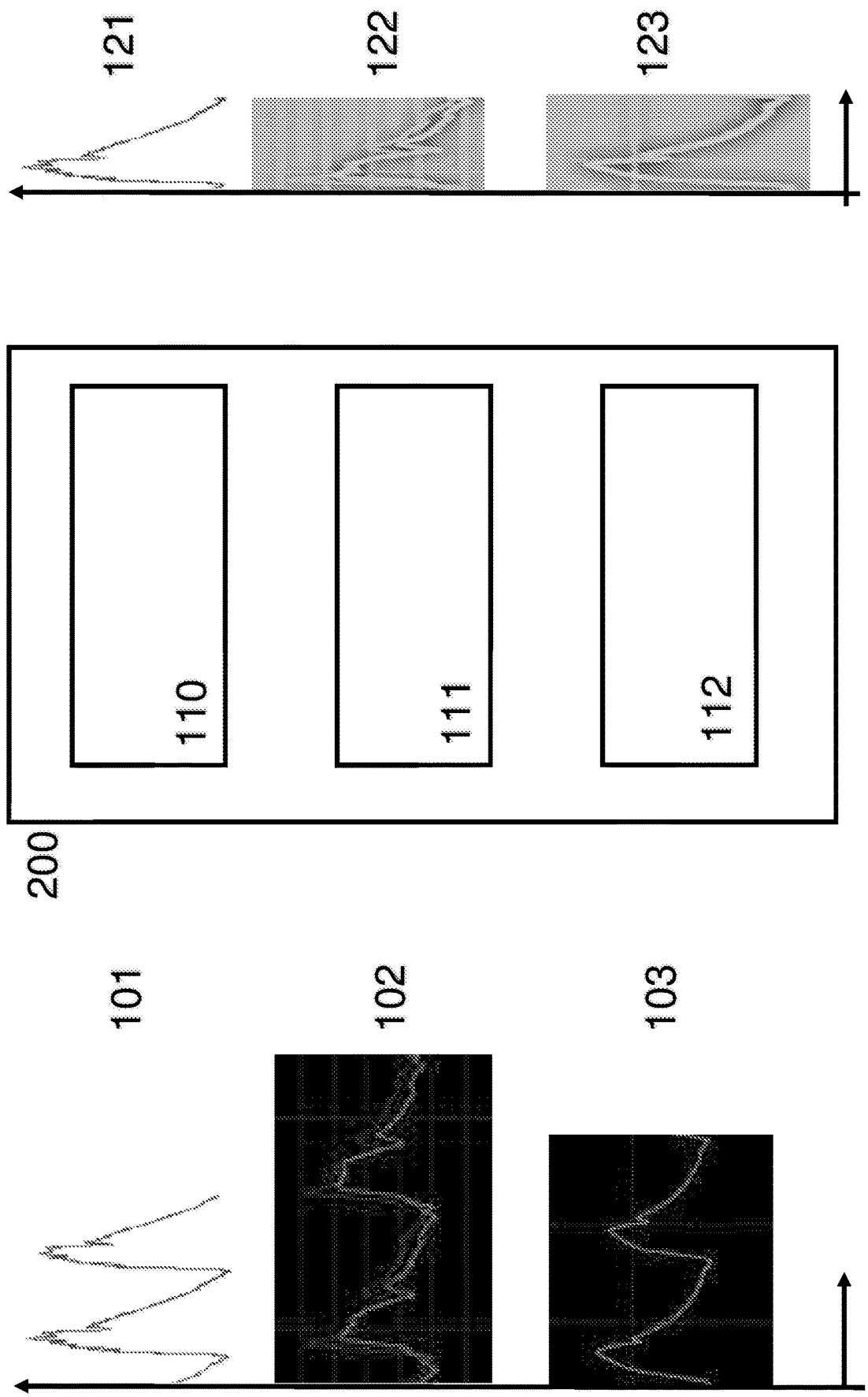
FIG. 22 illustrates a waveform detector embodying the present invention together with an illustrative input and illustrative output.

Another aspect of the present invention provides the waveform detector 200 as shown in FIG. 22 which can operate on: an image captured of a waveform; data from a data stream or data feed; or any other medium for representing a waveform. Using machine learning and object recognition, the waveform detector identifies, for example, a pressure waveform as an object usually from an image such as a trace 101, screen grab 102, 103 or photo of a trace. The recognised waveform is then available for extraction 110 (decluttering and isolating the waveform data), categorisation 111 (as a likely type of waveform: e.g. Pa or Pd waveform), normalisation 112 (scaling to a standard template with at least a standard timescale and potentially amplitude for training a system on). The standard waveform can also be saved. In the three examples shown in FIG. 22, the waveform detector 200 takes each of the three waveform images 101, 102, 103 and recognises predetermined points/datum such as the start of a period, end of a period and the location of the aortic notch. Other datum may also be used or identified. The waveform detector 200 transforms the image data as necessary to provide a standard output which can then be used to train the analyser 40 embodying the invention.

In the examples shown in FIG. 22, the waveform detector 200 recognises the waveforms in the images 101, 102, 103 and transforms them to conform to a standard template. This example provides a single period waveform 121, 122, 123 with standard peak to trough pixels and standard timescale.

The actual shape or profile of the waveform itself is valuable information in its own right and whilst measurements can be taken from the waveform trace itself and/or whilst measurements can be inferred or derived from the waveform trace, the profile, shape, characteristics of the waveform itself is information which the system trains itself on and uses, within the system, to weight outcomes, determine trend-matching and influence probabilities of a particular intervention being beneficial or not beneficial.

There is potential information to be gathered before the image is normalised such as the area under the trace and the actual period pre-normalisation and the actual amplitude pre-normalisation. This information can be captured by the waveform detector pre-normalisation and stored or associated with the waveform detector normalised output. The standard template may have one (as illustrated) period or multiple periods.

The waveform detector 200 adds to the current index-driven approach: current techniques look to identify treatment thresholds based on an index derived from pressure waveforms. Examples of this index include FFR, iFR or Pd/Pa. Whilst this approach simplifies assessment, it means that a significant proportion of the data is ignored. This could include the magnitude of the blood pressure, compliance related waveform changes, and attenuation of the aortic notch etc. The data ignored by an index-driven approach may be valuable. The incorporation of a waveform detector in the system embodying the invention advances the field by modelling all aspects of waveform changes and is able to relate those to potential treatment, risk analysis and outcomes. In addition to just looking at the waveform, the analyser 40 also takes into account multiple data sources—the broad spectrum of data including, by way of example, risk factors and demographic factors.

Interventions which are selectable by the treatment allocation module 70 depending on the probability associated with "Treat"/"no treat" of an arterial stenosis based on ischaemic prediction:
Treat=coronary revascularisation with either PCI (percutaneous coronary intervention), CABG (coronary artery bypass grafting).
No treat=no revascularisation, and the continuation of treatment with medical (i.e. drug) therapy.

The ischaemic prediction would be derived from the shape of the pressure waveforms and used to predict other measures of ischaemia from other standards in the training set (i.e. iFR, FFR, and blood flow).

Interventions which are selectable by the treatment allocation module 70 depending on the probability associated with "Treat"/"no treat" of an arterial stenosis based on mortality/morbidity prediction. The mortality/morbidity prediction would train the pressure waveform against known mortality and mortality predictors (i.e. MI, Death, Need for further treatment).

The analyser 40 offers up proposed outcomes trained on a dataset defined by the broad spectrum of data including real-world interventions/patient data.

Treat=coronary revascularisation with either PCI (percutaneous coronary intervention), CABG (coronary artery bypass grafting).
No treat=no revascularisation, and the continuation of treatment with medical (i.e. drug) therapy.

The analyser 40 can also determine probability models for other outcomes such as:
Focal disease=Treat—segment of disease with moderate-severe intensity
Diffuse disease=No treat—long segment of disease of mild-moderate intensity along the length of a vessel Other potential interventions include but are not limited to: balloons, sheaths, stents, closures, valvular interventions and sites for aforementioned; pacemaker, valve implantation, lead repositioning, do nothing, use certain pharma, move stent, move pacemaker lead, optimise position of valve implantation.

Examples of sensors or data sources 10 which provide data 20 to the database 100 include:

1) Physiological or pressure waveform detectors—these provide recordings of the aortic and pressure wire pressures;
2) ECG—this provides a recording of electrical activity over one or more cardiac cycles, from multiple vectors across the heart; and
3) Fluroscopy/Angiography—these provide images (x-ray) to assess structures in the body, for example, to identify the arteries, veins, cavities, and chambers.

The derived images/data is normalised so that the image dimensions are all the same. Portions of images which do not fit within pre-defined parameters can be blanked out from consideration.

Images of the pressure wave forms, ECG, Angiograms etc are all standardised to ensure that the image learning process in the analyser is based on standard dimensions.

Examples of the present invention produce effective results particularly where the analyser 40 is analysing medical or physiological data in the form of images such as analysing waveform-like data or traces and CT, MRI, X-ray and other physiological or medical image data.

Other techniques which can be analysed in the coronary medical field include:
the positioning of an aortic valve—predicting good outcome depending on whether the positioning of the valve in relation to the coronary arteries and left ventricle is sitting too high or too low;
the positioning of a pacing wire—risk analysis of pacing lead displacement—good position or bad position; and/or
identification and selection of the correct size valve, and make of valve for percutaneous valve implantation or stent in the case of arterial revascularization.

Examples of the claimed invention improves on previously available systems in broad terms because the system is trained on and across multiple data inputs and multiple data sources. In combination with the captured or sensed data, there is also an overlay of the historical or study data which colours the risk analysis to take into account a broad spectrum of data when arriving at the risk analysis. The data analysed by the analyser comprises both hard clinical data and measurement comparisons to deliver a unique scaling risk factor modifier.

The analyser 40 is trained to deliver risk analysis of a "Treat"/"no treat" of an arterial stenosis based on ischaemic prediction using the following profile:
Data capture (Waveforms, ECG, numerical demographic and risk factor profiling)
Outcome capture (Diffuse, Focal, Live, Die)
Data extraction
Data pre-processing
  Scaling
  Pixel Normalise—image dimension are all the same. Surround the images with black if not of the pre defined parameters
  Zero entering (every pixel has a scale between 0 and 1), single channel
  Down sampling to 227×227 pixels
Split in to training set and validation set.
Input to neural network
Training the neural network—against known treat/non treat decision-making
Validation against validation sets
Output node values The analyser 40 is trained to deliver risk analysis of a "Treat"/"no treat" of an arterial stenosis based on mortality/morbidity prediction using the following profile:

Data capture (Waveforms, ECG, numerical demographic and risk factor profiling)
Outcome capture (Diffuse, Focal, Live, Die)
Data extraction
Data pre-processing
  Scaling
  Pixel Normalise—image dimension are all the same. Surround the images with black if not of the predefined parameters
  Zero entering (every pixel has a scale between 0 and 1), single channel
  Down sampling to 227×227 pixels
Split in to training set and validation set.
Input to neural network
Training the neural network—against known CV events
Validation against validation sets
Out node values The analyser 40 is trained to deliver an identification of diffuse or focal disease using the following profile:

Data capture (Waveforms, ECG, numerical demographic and risk factor profiling)
Outcome capture (Diffuse, Focal, Live, Die)
Data extraction
Data pre-processing
  Scaling
  Pixel Normalise—image dimension are all the same. Surround the images with black if not of the pre defined parameters
  Zero entering (every pixel has a scale between 0 and 1), single channel
  Down sampling to 227×227 pixels
Split in to training set and validation set.
Input to neural network
Training the neural network—against known focal and diffuse categorised traces.
Validation against validation sets
Output node values When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A medical intervention control system for providing a risk analysis and influencing intervention action on a patient, the system comprising:
a database with a data set containing data from at least one data source comprising sensed data;
a waveform detector operable to identify a waveform from the at least one data source, extract the waveform, categorise the waveform, normalise the waveform to a predetermined format, determine waveform characteristics and parameters of the waveform, and populating the data set with waveform data;
a measurement module to derive subject data from the patient;
an analyser operable to analyse the subject data with respect to the data set comprising the sensed data and the waveform data and output an associated probability for each of one or more outcomes, wherein the associated probability is affected by an intervention, wherein the analyser takes the subject data derived from the patient and tests for outcomes and potential interventions which influence the outcomes;
an action and alert management module to provide feedback to an intervention allocation module and, for respective interventions, being operable to output a direct instruction to an intervention allocation module to perform an intervention or a direct instruction to an intervention allocation module to desist from performing an intervention; and
an intervention allocation module to perform an intervention or desist from an intervention depending on the direct instruction from the action and alert management module on the current patient.

2. The system according to claim 1, wherein the waveform is identified from the at least one data source comprising an image.

3. The system of claim 1, wherein the analyser builds up a probability matrix trained to deliver a risk analysis of various "treat"/"no treat" options based on trained data and the system delivers a risk analysis of what the risk is if the patient is treated with an option or the risk if the patient is not treated with a treatment option.

4. The system of claim 1, wherein the output of the action and alert management module includes a set of instructions relating to a respective intervention for the intervention allocation module.

5. The system of claim 1, wherein the intervention allocation module includes a medical robot operable to perform the intervention and at least one step of the intervention to be undertaken by the robot requires an authorisation input from a human user.

6. The system of claim 1, wherein subject data is sensed subsequent to an intervention to re-evaluate the patient's condition.

7. The system of claim 1, wherein the sensed data comprises: captured or sensed data points, waveforms or images obtained from sensing equipment such as electrocardiograms, coronary pressure wires and transducers, angiograms, ultrasonic transducers, coronary guidewire-mounted sensors to provide data on Fractional Flow Reserve—FFR, iFR (instant wave-free ratio (iFR) version of FFR), coronary flow reserve—CFR, the relationship between resting distal coronary pressure to aortic pressure ratio (Pd/Pa), medical insurance profiles and/or social media feeds,
wherein the data comprises inputs for predictive models in the analyser.

8. The system of claim 1, wherein the system further comprises a normaliser to normalise the data in the data set, wherein the normaliser fits the data into a standard template.

9. The system of claim 1, wherein the analyser comprises a plurality of analysers, one or more of which analyses the data from at least one of the data sources and attaches a probability model of likely outcomes for respective interventions.

10. The system according to claim 1, wherein a risk analysis assessment module is operable to provide a risk analysis based on the output of the analyser.

11. The system of claim 1, wherein the waveform detector is operable to transform image data of a waveform to provide a standard output which can then be used to train the analyser.

12. The system of claim 7, wherein probability values from each input of the inputs are stored in a matrix, where each value is iterated by further input from the fields to determine a series of probability node values for each of the inputs when used individually or when used in consort with other inputs and the series of node values determine the need for treatment, the probability of significant mortality and morbidity, risk analysis and the ability to discriminate between focal and diffuse disease and a probability is assigned to each outcome or potential intervention so as to then make a determination, potentially in consultation with a health professional or to better inform the practicing health professional about what outcomes or interventions to consider.

13. A method for providing a risk analysis and influencing intervention action on a patient, the method comprising:

establishing a database with a data set containing data from at least one data source comprising sensed data;

populating the data set with waveform data, wherein the waveform is extracted from a data source and normalised to a predetermined format;

deriving subject data from the patient;

testing the subject data for outcomes and potential interventions which influence the outcomes for the patient;

analysing the subject data with respect to the data set from the at least one data source and outputting an associated probability for respective outcomes, wherein the associated probability is affected by an intervention;

outputting, for respective interventions, a direct instruction to perform an intervention or a direct instruction to desist from performing an intervention; and performing the intervention or desisting from the intervention depending on the direct instruction.

14. The method of claim 13, further comprising:

identifying a waveform from the at least one data source;

determining waveform characteristics and parameters of the waveform, deriving subject data from the patient;

analyzing the subject data with respect to data from the at least one data source;

outputting an associated probability for each of one or more outcomes, wherein the associated probability is affected by an intervention;

testing the subject data for outcomes and interventions; and providing feedback and influence intervention or lack of intervention on the patient.

15. The system according to claim 1, wherein the data source further comprises study data.

16. The system according to claim 15, wherein the study data comprises: historic data which includes patient risk factors, patient demographics, associated clinical outcomes and results, historic sensed data and medical insurance profiles or social media feeds, Registry data; Actuarial risk tables; Clinical trial data; and/or Audit data.

* * * * *

UNITED STATES PATENT AND TRADEMARK OFFICE
CERTIFICATE OF CORRECTION

| | |
|---|---|
| PATENT NO. | : 11,387,001 B2 |
| APPLICATION NO. | : 16/957044 |
| DATED | : July 12, 2022 |
| INVENTOR(S) | : Jeremy James Walker |

It is certified that error appears in the above-identified patent and that said Letters Patent is hereby corrected as shown below:

On the Title Page

Item [73], insert --Cerebria Limited, Herts, United Kingdom--

Signed and Sealed this
Eleventh Day of October, 2022

Katherine Kelly Vidal
*Director of the United States Patent and Trademark Office*